United States Patent [19]
Yoon

[11] Patent Number: 5,478,317
[45] Date of Patent: Dec. 26, 1995

[54] RETRACTABLE SAFETY PENETRATING INSTRUMENT FOR PORTAL SLEEVE INTRODUCTION

[76] Inventor: InBae Yoon, 2101 Highland Ridge Dr., Phoenix, Md. 21131

[21] Appl. No.: 254,007

[22] Filed: Jun. 3, 1994

Related U.S. Application Data

[63] Continuation of Ser. No. 800,507, Nov. 27, 1991, abandoned.

[51] Int. Cl.⁶ ................................................. A61M 5/178
[52] U.S. Cl. .......................... 604/165; 604/157; 604/158; 604/264
[58] Field of Search ...................... 604/157, 158, 604/164, 165, 264, 274; 606/185

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,802,275 | 4/1989 | Haber et al. . |
| 4,817,603 | 4/1989 | Turner et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deneiga et al. . |
| 5,104,382 | 4/1992 | Brinkerhoff et al. . |
| 5,104,383 | 4/1992 | Schichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. . |

(List continued on next page.)

FOREIGN PATENT DOCUMENTS

| | | |
|---|---|---|
| 2544262 | 4/1977 | Germany . |
| 1435246 | 11/1988 | U.S.S.R. . |

Primary Examiner—Paul B. Prebilic

[57] ABSTRACT

A retractable safety penetrating instrument for introducing a portal sleeve into a cavity in the body includes a portal sleeve and a penetrating member disposed within the portal sleeve and supported in a manner to automatically move proximally from an extended position wherein a sharp distal end of the penetrating member protrudes from the portal sleeve to a retracted position wherein the sharp distal end of the penetrating member is protected in response to distal movement of the retractable safety penetrating instrument upon penetration into a cavity in the body. A retracting mechanism moves the penetrating member proximally and is normally locked in a position preventing proximal movement of the penetrating member and is released by distal movement of an operating member to trigger retraction of the penetrating member.

27 Claims, 6 Drawing Sheets

U.S. PATENT DOCUMENTS

| | | |
|---|---|---|
| 5,152,754 | 10/1992 | Plyley et al. . |
| 5,158,552 | 10/1992 | Borgia et al. . |
| 5,207,647 | 5/1993 | Phelps . |
| 5,226,426 | 7/1993 | Yoon . |
| 5,226,891 | 7/1993 | Bushatz et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |

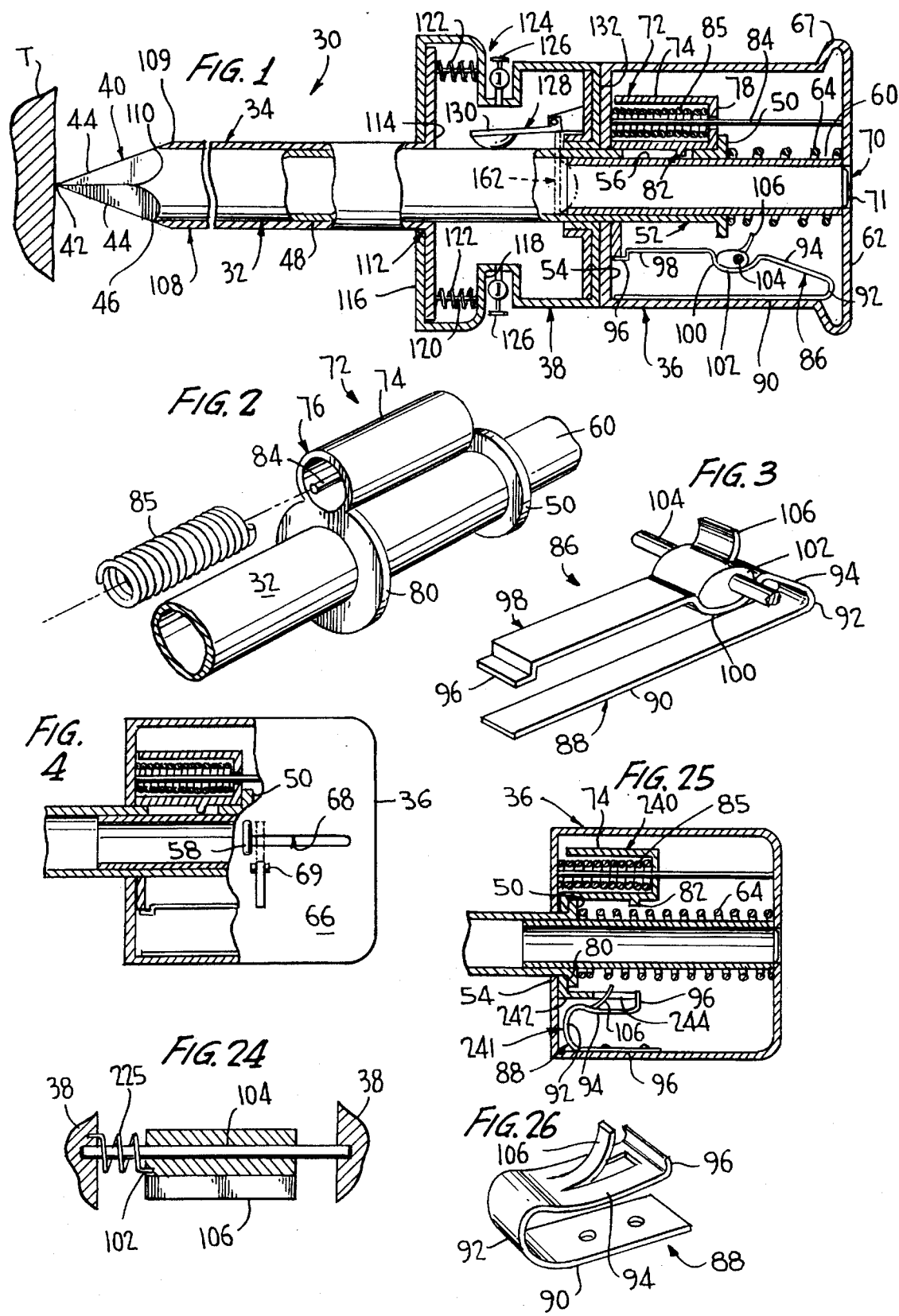

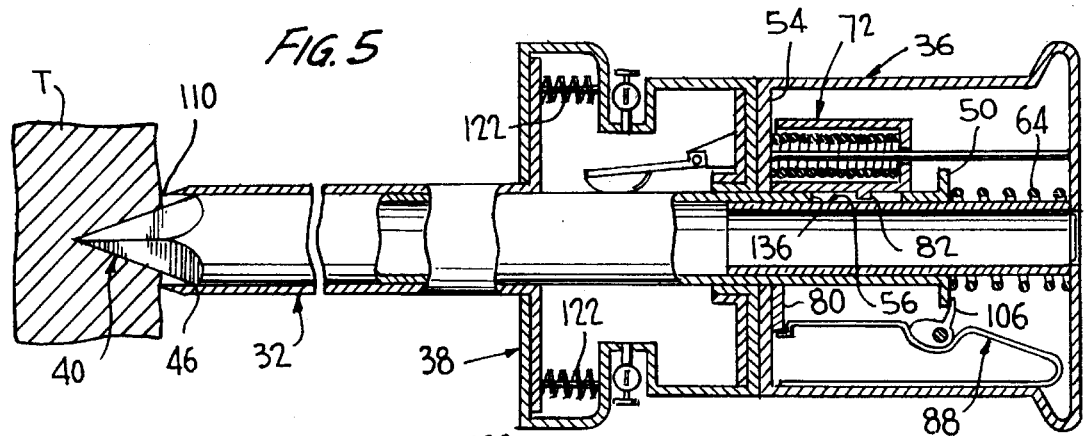
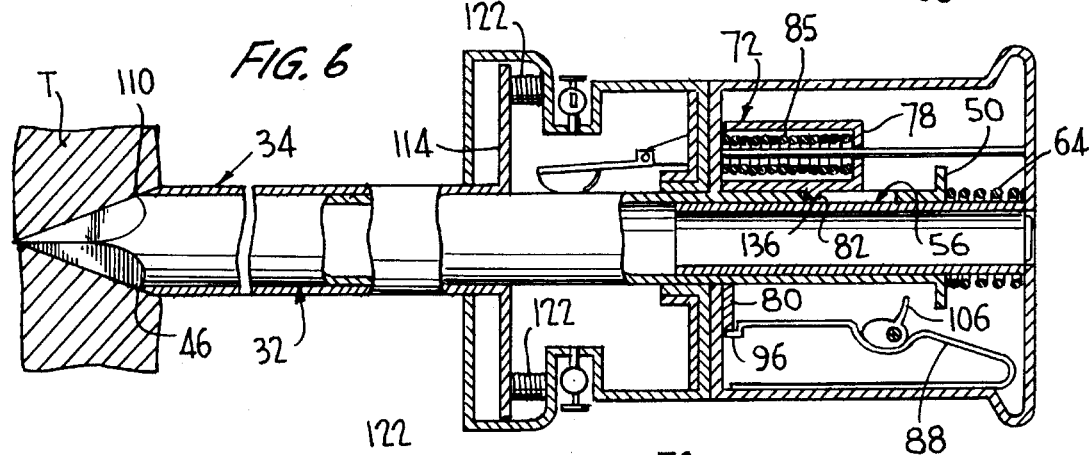
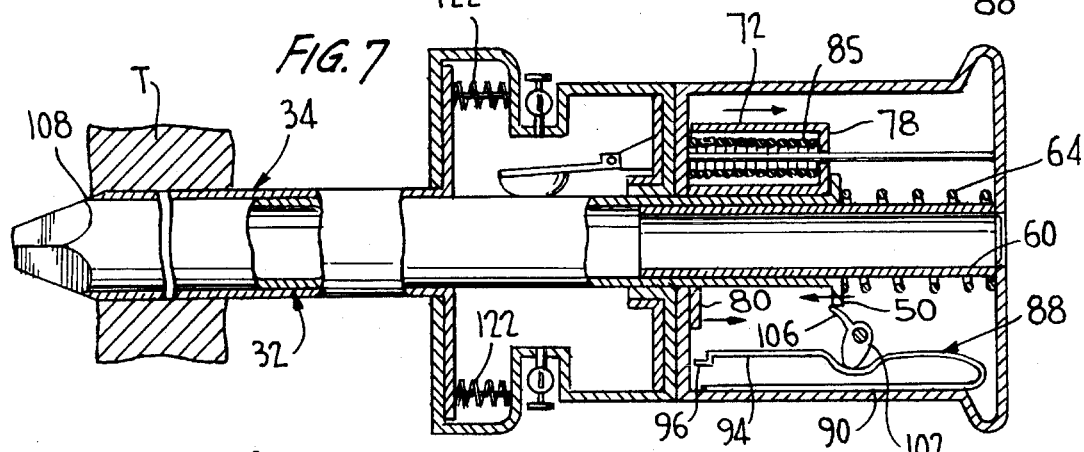
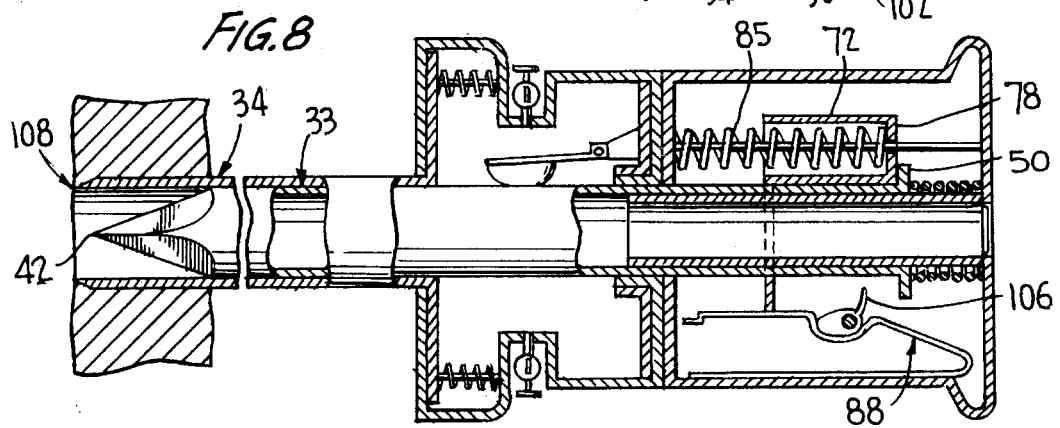

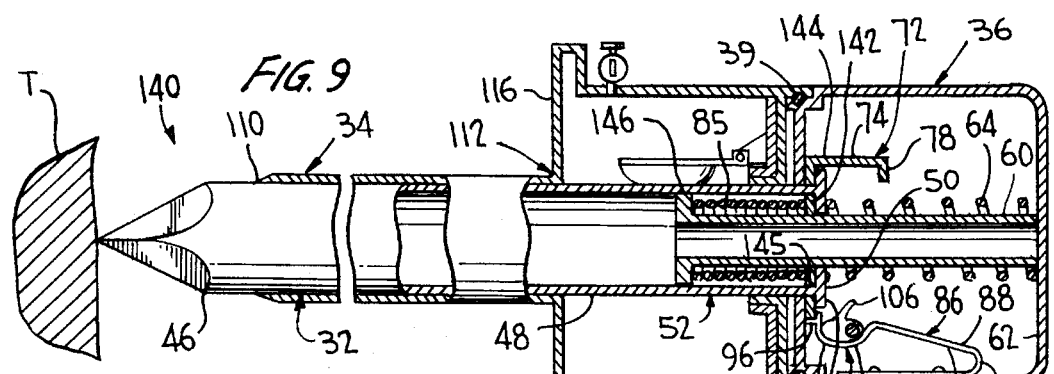
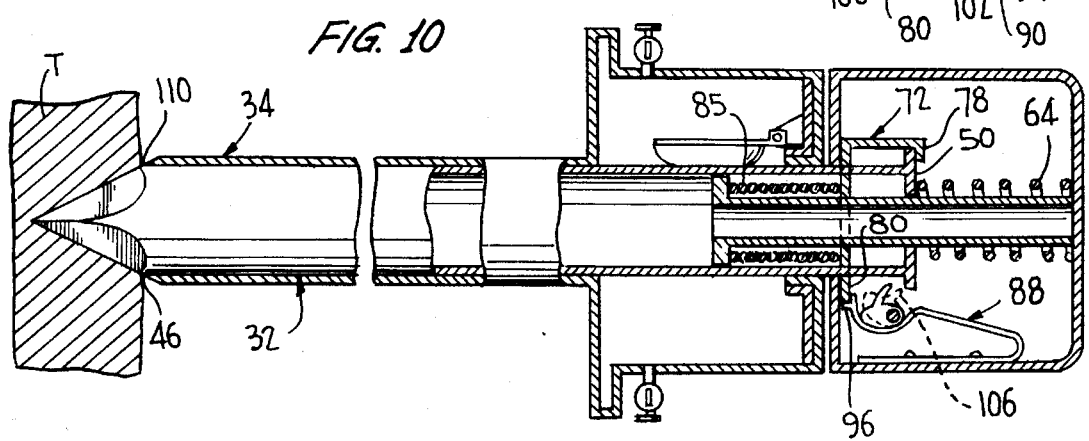
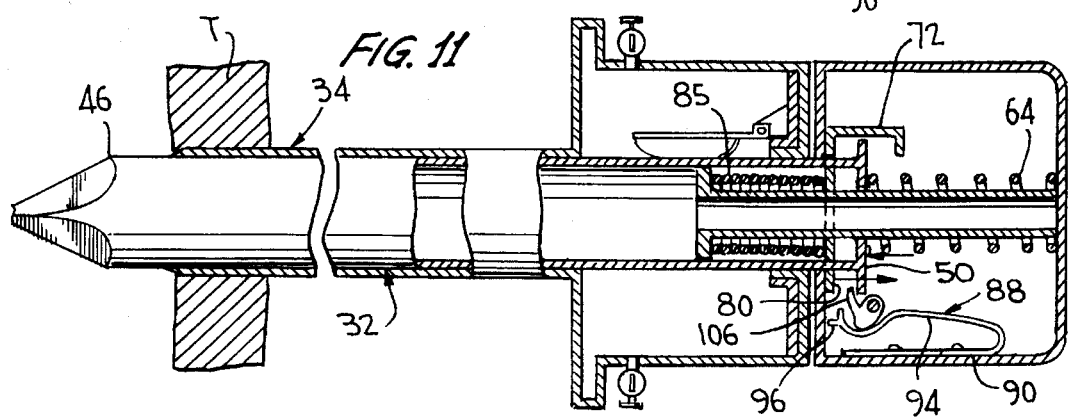
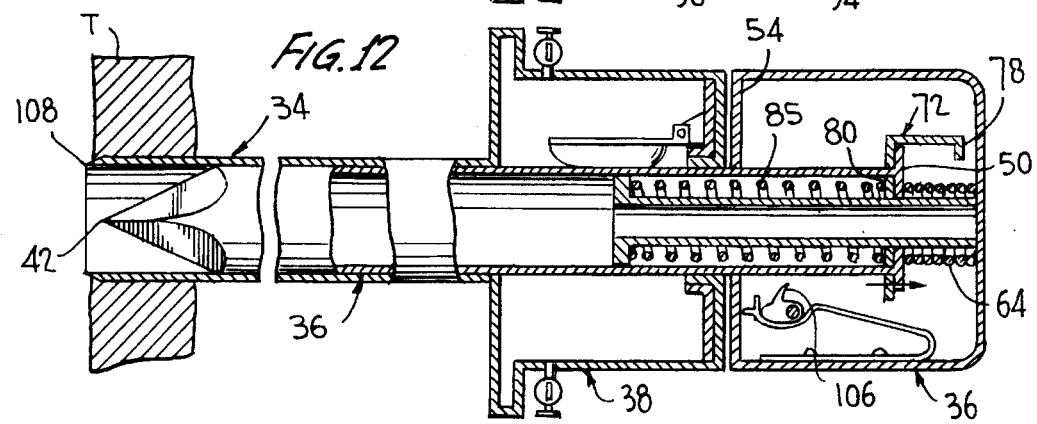

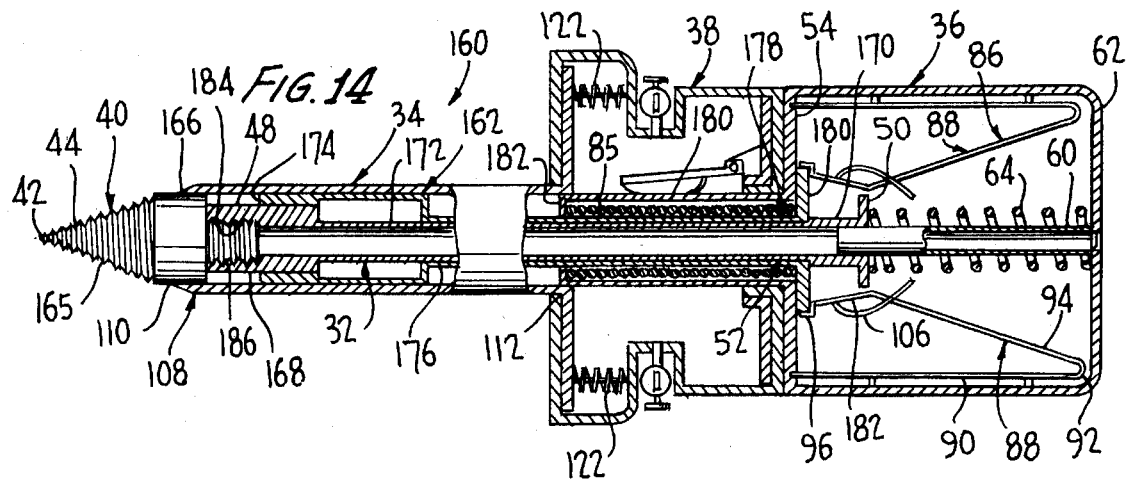
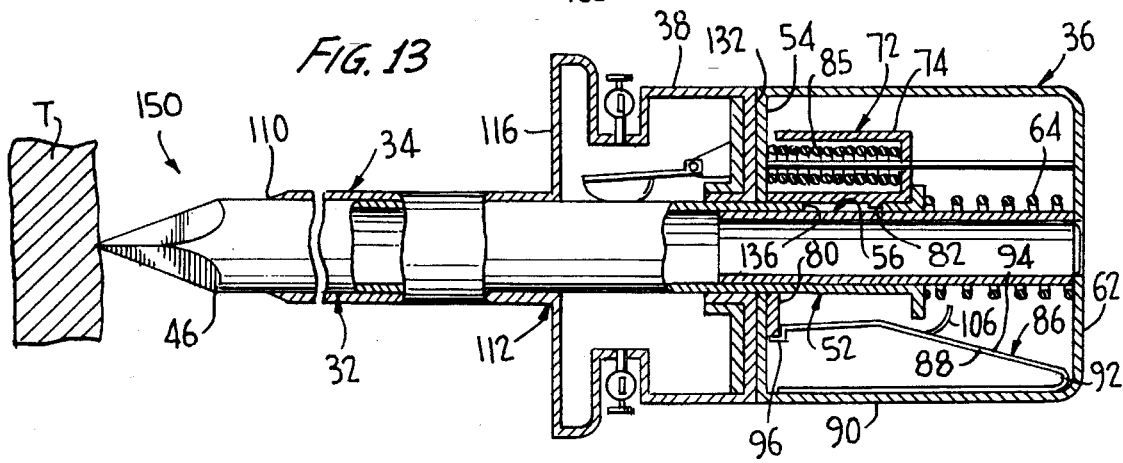
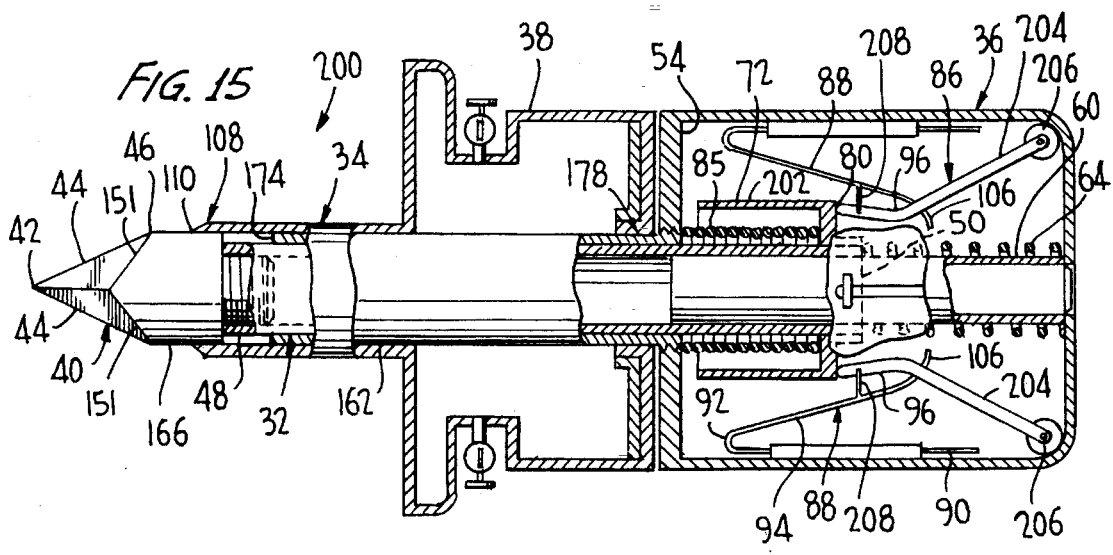

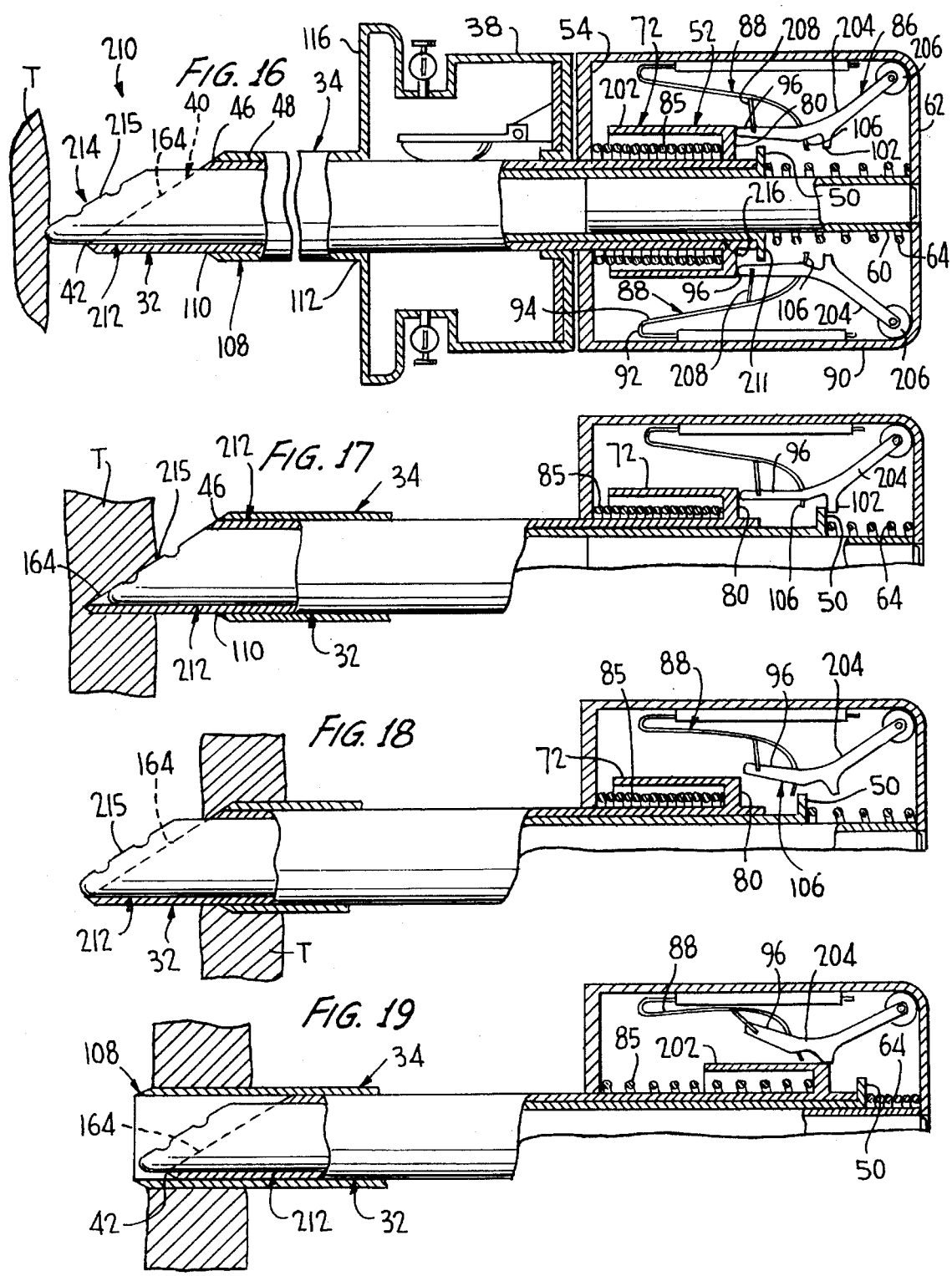

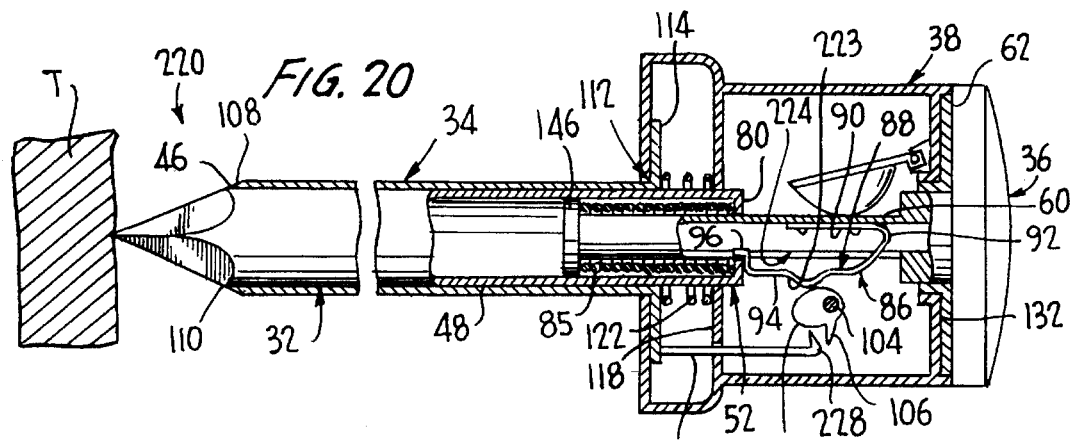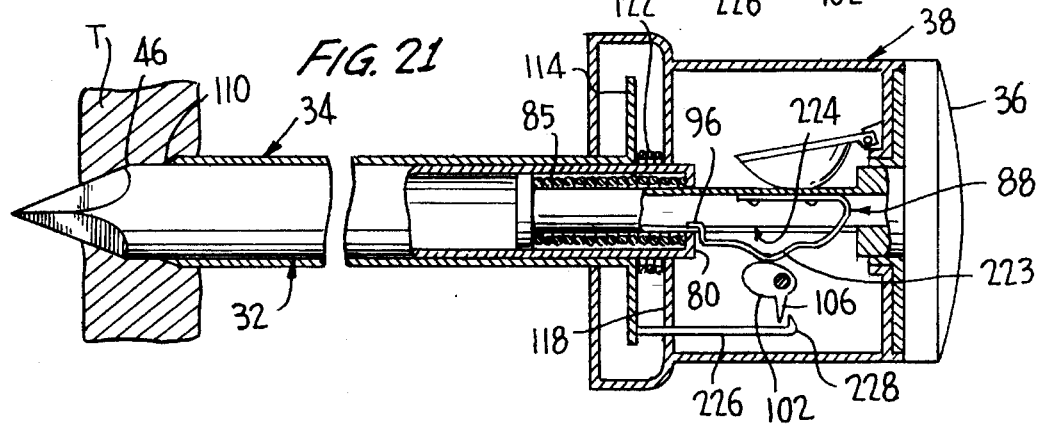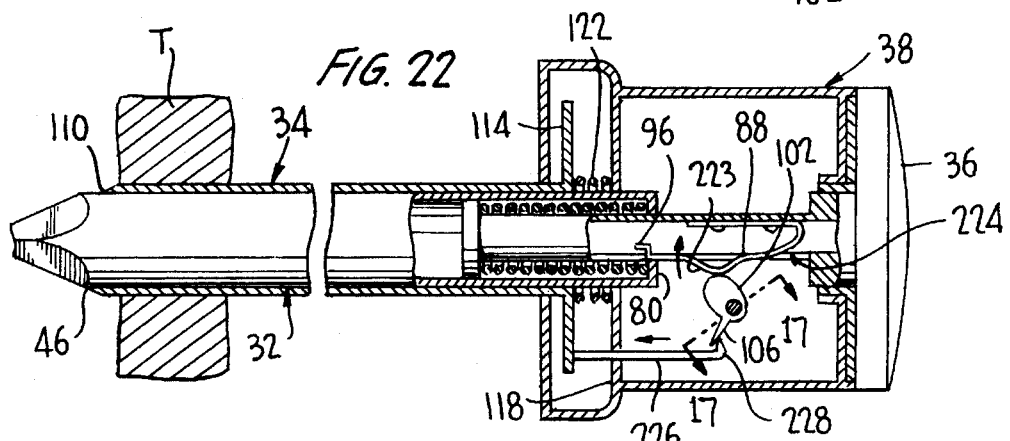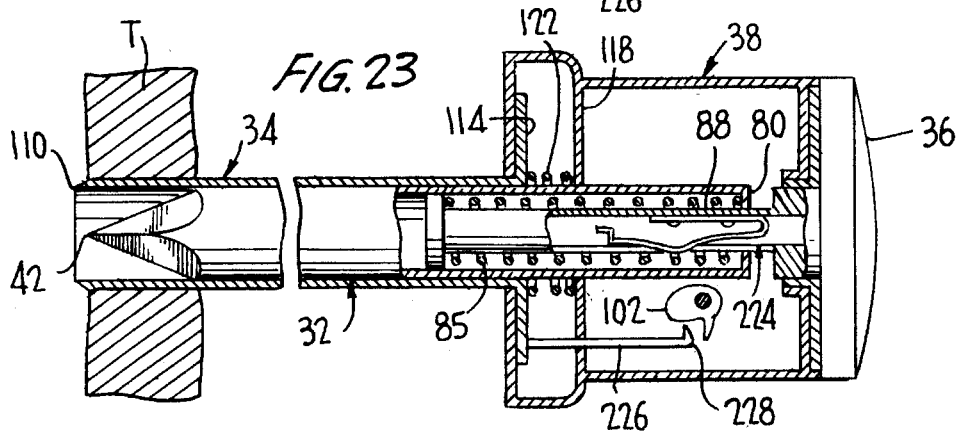

RETRACTABLE SAFETY PENETRATING INSTRUMENT FOR PORTAL SLEEVE INTRODUCTION

This application is a continuation of U.S. application Ser. No. 07/800,507, filed Nov. 27, 1991, and now abandoned.

BACKGROUND OF THE INVENTION

1. Field of the Invention

The present invention pertains to safety penetrating instruments and, more particularly, to safety penetrating instruments having portal sleeves for introduction into anatomical cavities and penetrating members with sharp tips for penetrating cavity walls and being automatically retractable upon penetration to protect tissue and organ structures within the cavities from the sharp tips of the penetrating members.

2. Discussion of the Prior Art

Penetrating instruments are widely used in medical procedures to gain access to anatomical cavities of various sizes; and, in particular, use of penetrating instruments has become an extremely popular and important first step in endoscopic, or least invasive, procedures to establish an endoscopic portal for many various procedures, most notably laparoscopy procedures, with access being established via a portal sleeve positioned during penetration into the cavity with the penetrating instrument. Such penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon, 4,601,710 to Moll and 4,654,030 to Moll et al are illustrative of such safety trocars. A trocar disposed within a portal sleeve and retractable within the sleeve in response to an electrical signal generated when force from tissue contact is removed from the sharp tip of the trocar is set forth in U.S. Pat. No. 4,535,773 to Yoon.

While prior art safety penetrating instruments are widely used, they suffer from many disadvantages when used in the procedures for which they are presently recommended; and, additionally, prior art safety penetrating instruments cannot be used in many procedures for which safety of penetration is highly desirable along with introduction of a portal sleeve. One of the disadvantages of prior art safety penetrating instruments is that the safety shields protrude from the sharp tips of the penetrating members to protect the sharp tips upon penetration through tissue of the cavity wall such that use in penetrating small or narrow anatomical cavities is not feasible. Another disadvantage of prior art safety penetrating instruments is that the safety shields can produce an irregular surface or profile with the portal sleeves and the sharp tips of the penetrating members during penetration of tissue resulting in increased resistance from tissue during penetrating of a cavity wall, trauma and damage to tissue and possible jamming and trapping of tissue.

SUMMARY OF THE INVENTION

Accordingly, it is a primary object of the present invention to overcome the above mentioned disadvantages of prior art safety penetrating instruments.

Another object of the present invention is to automatically retract a penetrating member of a safety penetrating instrument to a protected position in response to distal movement of the safety penetrating instrument after a distal end of a portal sleeve enters a body cavity.

A further object of the present invention is to arrange an operating member in a safety penetrating instrument such that movement of the operating member distally causes the penetrating member to retract to a protected, safe position within the instrument.

The present invention has an additional object of allowing safe introduction of portal sleeves into body cavities of very small size, such as synovial, pleural or pericardial cavities, for example, by automatically retracting a sharp tip of a safety penetrating instrument after the cavity is penetrated thereby minimizing the extension of the safety penetrating instrument into the cavity.

Yet another object of the present invention is to arrange a portal sleeve in a housing such that the portal sleeve can move proximally during penetration of a cavity wall and can move distally once penetration is completed to assure the distal end of the portal sleeve is positioned in the cavity.

An additional object of the present invention is to provide a method of safely penetrating various anatomical cavities by automatically retracting a penetrating member upon entry into a cavity in response to a mechanical distal movement of a component of a safety penetrating instrument.

A further object of the present invention is to provide a safety penetrating instrument including a portal sleeve and a distally biased penetrating member disposed within the portal sleeve and having a sharp tip retractable within the portal sleeve in response to movement of the penetrating member due to the distal bias upon penetration through tissue of a cavity wall.

It is also an object of the present invention to provide a safety penetrating instrument including a distally biased portal sleeve and a penetrating member disposed within the portal sleeve and having a sharp tip retractable within the portal sleeve in response to movement of the portal sleeve due to the distal bias upon penetration through tissue of a cavity wall.

Some of the advantages of the present invention over the prior art are that small or narrow anatomical cavities can be safely penetrated, an endoscopic portal can safely be introduced into anatomical cavities of various sizes to expand the use of least invasive procedures in many areas including, for example, the cardiac, brain, vascular, chest, genitourinary system and spinal fields, safe penetration of cavities can be accomplished with no parts of the safety penetrating instrument protruding beyond the sharp tip of the penetrating member as is particularly desirable where organ structures adhere to cavity walls, the retractable safety penetrating instrument encourages the use of a smooth, continuous penetrating motion by the surgeon thereby reducing trauma, tears and irregular surfaces in the tissue of the cavity wall, the retractable safety penetrating instrument can be used to penetrate anatomical cavities of the type containing organ structures that could be injured by contact with even a blunt instrument part such as a safety shield, with the use of a threaded distal tip on a penetrating member, penetration of the narrowest of anatomical cavities can be achieved in a safe manner in view of the gradual advancement of the penetrating member coupled with immediate automatic retraction of the penetrating member upon entry of the distal tip into the cavity, safe penetration is achieved while permitting injection or evacuation of fluids, a single puncture can be used for both insufflation and forming an endoscopic portal thereby simplifying diagnostic and surgical procedures, trauma and damage to tissue is minimized, tissue jamming and trapping is avoided and safety penetrating instruments according to the present invention can be inexpensively manufactured to be reusable or disposable for universal use.

The present invention is generally characterized in a retractable safety penetrating instrument for introducing a portal sleeve into a cavity in the body including a penetrating member supported in a manner to automatically move proximally from an extended position protruding from a portal sleeve to a safe retracted position in response to distal movement of the retractable safety penetrating instrument. The retraction of the penetrating member can be responsive to distal movement of the penetrating member, the portal sleeve or any other operating member, such as tubes or probes mounted outside or inside of the penetrating member. Retraction of the penetrating member is caused by a strong bias spring that is normally locked in a compressed state by a latch and is released by the distal movement of the operating member to trigger the retraction of the penetrating member. The latch and trigger are spring loaded to normally lock the penetrating member against retraction and to be moved out of locking engagement by flexing of the spring via movement of a cam, an off-center rotating member or a leaf of a spring in response to the distal movement.

These and other objects and advantages of the present invention will become apparent from the following description of the preferred embodiments taken in conjunction with the accompanying drawings.

BRIEF DESCRIPTION OF THE DRAWINGS

FIG. 1 is a broken side view, partly in section, of a retractable safety penetrating instrument according to the present invention.

FIG. 2 is a perspective view of a retracting mechanism for the retractable safety penetrating instrument of the present invention.

FIG. 3 is a perspective view of a locking and releasing mechanism for the retractable safety penetrating instrument of the present invention.

FIG. 4 is a broken view, partly in section, of a hub for the retractable safety penetrating instrument of the present invention.

FIGS. 5, 6, 7 and 8 are broken side views, partly in section, illustrating sequential stages of the locking, releasing and retracting operations of the retractable safety penetrating instrument of FIG. 1 and showing the corresponding positions of the penetrating member relative to the portal sleeve during penetration of tissue of a cavity wall.

FIG. 9 is a broken side view, partly in section, of a modification of a retractable safety penetrating instrument according to the present invention.

FIGS. 10, 11 and 12 are broken side views, partly in section, illustrating sequential stages of the locking, releasing and retracting operations of the retractable safety penetrating instrument of FIG. 9 and showing the corresponding positions of the penetrating member relative to the portal sleeve during penetration of tissue of a cavity wall.

FIG. 13 is a broken side view, partly in section, of a further modification of a retractable safety penetrating instrument according to the present invention.

FIG. 14 is a broken side view, partly in section, of another modification of a retractable safety penetrating instrument according to the present invention.

FIG. 15 is a broken side view, partly in section, of an additional modification of a retractable safety penetrating instrument according to the present invention.

FIG. 16 is a broken side view, partly in section, of a further modification of a retractable safety penetrating instrument according to the present invention.

FIGS. 17, 18 and 19 are broken side views, partly in section, illustrating sequential stages of the locking, releasing and retracting operations of the retractable safety penetrating instrument of FIG. 16 and showing the corresponding positions of the penetrating member relative to the portal sleeve during penetration of tissue of a cavity wall.

FIG. 20 is a broken side view, partly in section, of a further modification of a retractable safety penetrating instrument according to the present invention.

FIGS. 21, 22 and 23 are broken side views, partly in section, illustrating sequential stages of the locking, releasing and retracting operations of the retractable safety penetrating instrument of FIG. 20 and showing the corresponding positions of the penetrating member relative to the portal sleeve during penetration of tissue of a cavity wall.

FIG. 24 is a cross-sectional view taken along line 24—24 of FIG. 22.

FIG. 25 is a broken sectional view of a hub of another modification of a retractable safety penetrating instrument of the present invention.

FIG. 26 is a perspective view of the locking and releasing member of FIG. 25.

DESCRIPTION OF THE PREFERRED EMBODIMENTS

A retractable safety penetrating instrument 30 according to the present invention is illustrated in FIG. 1 and includes an elongate penetrating member 32, a portal sleeve 34 concentrically disposed around penetrating member 32, a hub 36 mounting penetrating member 32 and a housing 38 mounting portal sleeve 34. The hub 36 can be latched to housing 38 with the use of any suitable releasable mechanism, such as ball detents 39 shown in FIG. 9, allowing the hub to be removed from the housing withdrawing the penetrating member from the portal sleeve. Accordingly, the retractable safety penetrating instrument 30 can be considered to be formed of a portal unit and a penetrating member unit, the portal unit including portal sleeve 34 and housing 38 and the penetrating member unit including penetrating member 32 and hub 36.

Penetrating member 32 is preferably made of stainless steel with a cylindrical body having an outer diameter dependent upon the surgical procedure to be performed and the anatomical cavity to be penetrated. The penetrating member 32 has a distal end 40 terminating at a sharp tip 42 for penetrating anatomical tissue. The distal end 40 can have various configurations; and, as shown in FIG. 1, the distal end 40 is formed as a trocar with a pyramidal shape defined by equally spaced end surfaces or facets 44 tapering distally to sharp tip 42 and terminating proximally at scalloped edges or junction 46 joining the facets to an elongated, cylindrical body 48. Cylindrical body 48 extends proximally from junction 46 to an operating member or flange 50 at a proximal end 52 of the penetrating member, the proximal end 52 being disposed in hub 36 with cylindrical body 48 passing through an aperture in a front wall 54 of the hub 36. A longitudinal slot 56 parallel with a longitudinal axis of the penetrating member is formed in cylindrical body 48 to be disposed in hub 36; and, as shown in FIG. 4, a knob 58 is threadedly secured along the periphery of flange 50. The proximal end 52 of the penetrating member is hollow to be mounted on a cylindrical member or tube 60 extending distally from an end wall 62 of hub 36 and into the hollow proximal end 52 of the penetrating member. A helical coil spring 64 is disposed around tube 60 and mounted in compression between flange 50 and end wall 62 to bias the penetrating member in a distal direction. Cylindrical body 48 can be hollow or tubular along the length of the penetrating member 32 or the cylindrical body can be partly hollow or tubular depending upon manufacturing techniques utilized and the construction of the distal end 40 of the penetrating member. While the distal end of the penetrating member is shown having a trocar configuration, the distal end configuration can have other solid geometric configurations, such as conical or threaded configurations as shown in FIG. 14; and other types of penetrating members can be used with the retractable safety penetrating instrument, such as the tubular or cannulated penetrating member shown in FIG. 16.

Hub 36 is preferably made of plastic to reduce cost and has an external configuration to cooperate with housing 38 to be easily grasped with one hand for use in penetrating tissue. Hub 36 can be substantially rectangular in cross-section including four side walls extending from front wall 54 to end wall 62 with one side wall, indicated at 66 in FIG. 4, having a slot 68 therein disposed parallel with a longitudinal axis of the safety penetrating instrument and slidably receiving knob 58. A lock 67 is mounted externally along wall 66 on a hinge 69 such that the lock 67 can be pivoted between an unlocked position wherein the lock does not block movement of knob 58 along slot 68 and a locked position shown in broken lines at 71 wherein the lock is disposed transverse to slot 68 abutting a proximal face of knob 58 to block proximal movement of the knob and, therefore, the penetrating member. The side walls of the hub 36 can be flared as shown in FIG. 1 at 67 providing a flared external profile adjacent end wall 62. A valve assembly 70, such as rotatable valve 71, is provided in end wall 62 of the hub in alignment with the lumen of tube 60 to allow passage of fluid therethrough for additional confirmation of cavity penetration via leakage detection and for irrigation and aspiration when the penetrating member is hollow thereaolong and is provided with an aperture at distal end 40 establishing fluid communication between the lumen of tube 60 and an anatomical cavity.

As shown in FIGS. 1 and 2, a retracting mechanism 72 is mounted on the proximal end 52 of the penetrating member 32 and includes a cylindrical rail 74 having an open distal end 76 and a proximal end closed by an abutment wall 78 and a plate 80 extending from distal end 76 in a direction perpendicular with a longitudinal axis of the rail 74. Cylindrical body 48 of the penetrating member 32 extends through an opening in plate 80 such that a pin 82 on an external surface of rail 74 is received in slot 56 of cylindrical body 48. Penetrating member 32 is biased distally by spring 64 such that flange 50 of the penetrating member is biased against abutment wall 78 and pin 82 is positioned at the proximal end of the slot 56. A connecting bar 84 has ends secured to the front and end walls 54 and 62 of hub 36, the bar 84 passing longitudinally through the rail 74 via an opening in abutment wall 78. A helical retracting spring 85, stronger than spring 64, is disposed around connecting bar 84 within the rail 74 and is mounted in compression between front wall 54 of the hub and abutment wall 78 of the rail to bias the rail and, via abutment with flange 50, the penetrating member in a proximal direction.

A locking and releasing mechanism 86 for the retracting mechanism 72 is illustrated in FIGS. 1 and 3 and includes a latch or locking spring 88 having a substantially flat base 90 secured to a side wall of hub 36 and terminating proximally in a bend 92 adjacent end wall 62 and an arm 94 joined to bend 92 and extending angularly, distally therefrom in the direction of the longitudinal axis. A bent locking finger 96 on a distal end 98 of the arm 94 engages plate 80 and holds the plate against front wall 54 of the hub to prevent movement of the retracting mechanism 72 in a proximal direction. Latch 88 has a curved section 100 between bend 92 and distal end 98, the curved section 100 curving toward the base 90 to define a clearance, and a releasing or trigger member such as an off-center pivot or cam 102 is mounted in the clearance. Cam 102 is rotatable on a pin 104 extending transverse to arm 94 and having ends secured to side walls of the hub, pin 104 passing through cam 102 off-center with a central longitudinal axis of the cam. A trigger or leaf 106 curved in a distal direction extends from a proximal portion of cam 102 in the direction of the longitudinal axis, the cam 102 being positioned by arm 94 such that the trigger 106 will be disposed in a rest position proximally of flange 50 in the path of movement of the flange along tube 60 with finger 96 engaging plate 80 as shown in FIG. 1. Although arm 94 biases cam 102 to the rest position, a spring (not shown) can be disposed around pin 104 and secured to a side wall of hub 36 and the cam 102, respectively, with a torsional bias to bias the cam to the rest position. The latch can be mounted at any suitable location on the hub and provided with a configuration to act as a stop or abutment to prevent proximal movement of the retracting mechanism and to be actuated or released by a trigger. The latch and trigger can be made as one piece or multiple pieces dependent upon the hub construction and the operating member for engaging the trigger, flange 50 in retractable safety penetrating instrument 30.

Portal sleeve 34 is preferably made of a cylindrical length of stainless steel or other suitable, medically acceptable, plastic or metal material and can be rigid or flexible and transparent or opaque. The portal sleeve has a distal end 108, that can be angled or beveled as shown at 109 in FIG. 1, terminating at a peripheral edge 110 disposed in substantial alignment with junction 46, such that the distal ends of the portal sleeve and the penetrating member present a substantially smooth profile to facilitate tissue penetration as shown in FIG. 1. The portal sleeve has a proximal end 112 with a flange 114 thereon disposed in housing 38, the proximal end 112 passing through an opening in a front wall 116 of the housing.

Housing 38 is preferably made of plastic to reduce cost and has a configuration in cross-section corresponding to the cross-sectional configuration of hub 36 with a flared intermediate wall 118 proximally spaced from front wall 116 producing a flared external profile facilitating grasping during use. Connecting bars 120 have ends secured to front wall 116 and intermediate wall 118, respectively, with the bars passing through openings in flange 114 on diametrically opposite sides of the portal sleeve 34. Helical springs 122 are disposed around the bars 120 and are mounted in compression between flange 114 and intermediate wall 118 to bias the portal sleeve in a distal direction with flange 114 abutting front wall 116. Recesses 124 are formed in the housing 38 proximally of intermediate wall 118 and have a size and configuration to receive ball-type stop cocks 126, respectively, in a position such that the stop cocks are protected from inadvertent contact which could cause breakage or malfunction. A valve assembly 128 is mounted in housing 38 to control flow through the portal sleeve and the housing once the penetrating member unit is removed therefrom. The valve assembly 128 can have any acceptable configuration and, as shown, includes a flapper valve 130 biased to close off and seal an opening in an end wall 132 of the housing 38 as shown in broken lines at 162 in FIG. 1. The portal sleeve has an outer diameter typically ranging in size from 5 mm to 12 mm and an inner diameter sized to closely receive the outer diameter of the penetrating member such that there is a minimal gap or space between the portal sleeve and the penetrating member.

In order to assemble the retractable safety penetrating instrument 30, the proximal end 52 of the penetrating member 32 is assembled in hub 36 as shown in FIG. 1 with plate 80 of retracting mechanism 72 held against front wall 54 of hub 36 by latch 88 against the proximal bias of retracting spring 85, penetrating member 32 being biased distally by spring 64 such that operating flange 50 abuts abutment wall 78 and is disposed distally of trigger 106. The pin 82 is disposed at the proximal end of slot 56; and, accordingly, penetrating member 32 will be prevented from rotating relative to retracting mechanism 72 such that angular alignment of the distal ends of the penetrating member and portal sleeve is assured. The penetrating member unit formed by the penetrating member 32 and the hub 36 is then combined with the portal unit by passing the penetrating member through the housing 38 via the opening in end wall 132, while simultaneously opening valve 130, and through the portal sleeve 34. With the front wall 54 of hub 36 abutting the end wall 132 of housing 38, the peripheral edge 110 of the portal sleeve 34 will be disposed substantially in alignment with the junction 46 to facilitate penetration of tissue by the penetrating member and to minimize tissue jamming and trapping as shown in FIG. 1.

In a method of operation for the retractable safety penetrating instrument, the latch 88 is normally in the position shown in FIG. 1 with trigger 106 in the rest position and finger 96 engaging a proximal face of plate 80 such that the retracting mechanism 72 can not move proximally and is, therefore, locked with the plate held against front wall 54 of hub 36. Springs 64 and 122 are normally in the position shown in FIG. 1 such that the penetrating member 32 and portal sleeve 34 are biased distally with peripheral edge 110 of the portal sleeve substantially aligned with junction 46 to present a substantially smooth profile as shown in FIG. 1 just prior to penetration of tissue T of an anatomical cavity wall. When tissue T is to be penetrated, the hub 36 and housing 38 are gripped in one hand and the safety penetrating instrument is forced into the tissue T as shown in FIG. 5. The penetrating member 32 will move proximally against the distal bias of spring 64 due to the proximal force from tissue contact at the distal end 40 of the penetrating member such that peripheral edge 110 of the portal sleeve 34 will protrude distally of junction 46 a short distance. Operating flange 50 will have moved proximally within hub 36 but remain positioned distally of trigger 106. Once the peripheral edge 110 abuts an external surface, of the tissue T, portal sleeve 34 will move proximally against the distal bias of springs 122 due to the proximal force from tissue contact while the penetrating member 32 will continue to move proximally until a distal end 136 of the slot 56 abuts pin 82 thusly providing a positive stop limiting proximal movement of the penetrating member as shown in FIG. 6. As penetrating member 32 continues to move proximally, operating flange 50 moves proximally past trigger 106, the operating flange being disposed proximally of the trigger when distal end 136 of the slot 56 abuts pin 82. During movement past the trigger 106, flange 50 urges the trigger clockwise looking at FIG. 6; however, this movement does not disengage the latch 88 from the plate 80 and the trigger returns to the rest position as soon as the operating flange 50 has moved proximally therepast. Portal sleeve 34 will move proximally with springs 122 being compressed between flange 114 and intermediate wall 118 to provide a positive stop limiting proximal movement of the portal sleeve. Accordingly, when the portal sleeve 34 and penetrating member 32 have moved proximally the full amount, as limited by the positive stops, the peripheral edge 110 of the portal sleeve will be substantially aligned with junction 46 to present a smooth profile during penetration of the tissue T as shown in FIG. 6, the portal sleeve and the penetrating member being stable and moving together through the tissue. In other words, the distance of travel for flange 114 of portal sleeve 35 is the same as the distance of travel for the distal end 136 of slot 56 in response to force from tissue contact at a distal end of the retractable safety penetrating instrument. Once the distal end 108 of the portal sleeve 34 has entered the anatomical cavity, as shown in FIG. 7, such that the force from tissue contact is removed from the distal end of the retractable safety penetrating instrument, the penetrating member and portal sleeve will be moved distally due to the distal bias of springs 64 and 122, respectively, as shown in FIG. 7. As the penetrating member 32 moves distally, operating flange 50 moves distally to engage the trigger 106 and pull the trigger distally causing the cam 102 to rotate counterclockwise looking at FIG. 7. With counterclockwise rotation, cam 102 is forced against the latch 88 in a direction outwardly from the longitudinal axis moving arm 94 outwardly in the direction of base 90 and releasing finger 96 from engagement with plate 80 of the retracting mechanism 72. Once released, the retracting mechanism 72 will move proximally due to strong retracting spring 85 overriding the distal bias of the spring 64, and the retracting mechanism 72 will carry the penetrating member 32 proximally along the tube 60 due to the abutment of operating flange 50 with abutment wall 78, the tube 60 guiding proximal movement of the penetrating member. With the penetrating member 32 moved proximally by the retracting mechanism 72, the sharp tip 42 of the penetrating member 32 is retracted within the distal end 108 of the portal sleeve 34 and the operating flange 50 is positioned proximally of trigger 106, the trigger 106 having returned to the rest position as shown in FIG. 8. When it is desired to reset the retractable safety penetrating instrument for further use, the knob 58 is grasped and manually moved distally along the slot 68 in hub 36 moving the penetrating member 32 and the retracting mechanism 72 distally past the trigger 106 until the plate 80 abuts the front wall 54 of the hub 36 and is held thereagainst by finger 96 of the latch 88.

By varying the axial position of trigger 106 in the path of movement of the operating flange 50, the distance that the penetrating member can move distally before operating flange 50 releases the retracting mechanism 72 upon penetration into an anatomical cavity can be controlled. In other words, the distance that the sharp tip 42 of the penetrating member 32 is allowed to protrude beyond the peripheral edge 110 of the portal sleeve 34 upon penetration into an anatomical cavity can be varied or adjusted by positioning the trigger 106 to be disposed distally a greater or lesser distance from the operating flange after the flange has moved proximally during penetration. Accordingly, with the trigger 106 positioned distally of flange 50 a lesser distance, the penetrating member 32 will move distally a relatively shorter distance before retracting mechanism 72 is released and, with the trigger 106 positioned distally of flange 50 a greater distance, the penetrating member 32 will move distally a relatively greater distance before the operating flange triggers the retracting mechanism.

Although springs 64 and 122 are shown as coil springs, other types and configurations of springs as well as various other devices can be utilized to bias the penetrating member and the portal sleeve in a distal direction. Similarly, retracting spring 85 need not be a coil spring and can be replaced with various types and configurations of springs as well as various other devices for biasing the retracting mechanism in a proximal direction. It will be appreciated that the penetrating member, the portal sleeve and the retracting mechanism can be biased in many ways and that springs 64, 122 and 85 can be replaced with various devices, including flexible, compressible and resilient devices, capable of applying a directional biasing force. Although the portal sleeve 34 is shown as being biased by a pair of springs 122, a single spring or biasing device can be employed. For example, housing 38 can be constructed such that intermediate wall 118 extends inwardly to the outer diameter of the penetrating member 32, and a single spring can be disposed around the penetrating member and maintained in compression between flange 114 and intermediate wall 118 to bias the portal sleeve 34 in a distal direction.

The positive stop can include a pin and slot arrangement with the pin on the rail or on the inner tube as well as other positive stop construction, and the positive stop can be provided at the distal or proximal end of the retractable safety penetrating instrument.

Rail 74 can have various cylindrical and non-cylindrical configurations; and, in simplified form, the rail 74 can be formed from opposing, parallel, flat sides joined by abutment wall 78 with plate 80 extending perpendicularly from one of the flat sides. Additionally, plate 80 can have various surface configurations, such as circular, rectangular and square, and can be provided with an extension or ledge extending perpendicularly therefrom in a proximal direction with the finger 96 engaging this ledge to prevent proximal movement of the retracting mechanism 72. The distance that the ledge extends proximally form the plate 80 can be varied to accommodate locking springs of various lengths and configurations and to control the distance that knob 58 must be slid in slot 68 before the finger 96 will engage the retracting mechanism 72 when resetting the retractable safety penetrating instrument.

It will be appreciated that knob 58 is shown by way of example, and that many other types of knobs or handles can be employed for resetting the retractable safety penetrating instrument. As a further example, an L-shaped handle can be attached to flange 80 allowing the slot 68 to be located at various other positions along the side walls of the hub 36 and not only the central position shown in FIG. 4.

Where it is desired to lock the penetrating member 32 relative to the portal sleeve 34 such that the penetrating member 32 does not retract upon penetration into the anatomical cavity, lock 67 can be pivoted 180° from the unlocked position preventing proximal movement of the penetrating member 32 such that the retracting mechanism cannot be released. It will be appreciated that lock 67 is shown by way of example and that other locking devices can be utilized to prevent proximal movement of the penetrating member against the distal bias of spring 64.

Numerous other types of releasing or trigger members can be utilized in addition to cam 102 for releasing or disengaging the latch 88 from the retracting mechanism 72. The locking and releasing mechanism 86 can be of multi-part construction or of integral, unitary construction. Various types of actions including camming, bending, buckling and spring actions can be employed for releasing the latch 88 from the retracting mechanism.

A modification of a retractable safety penetrating instrument is shown in FIG. 9 at 140. The retractable safety penetrating instrument 140 includes penetrating member 32 having cylindrical body 48 terminating proximally at operating member or flange 50 defining an internal shoulder 142 extending radially inwardly from the cylindrical body 48 to be disposed around an opening receiving tube 60 passing into the hollow proximal end 52 of the penetrating member 32. Retracting mechanism 72 includes rail 74 having a side 144 extending perpendicularly from plate 80 in a proximal direction and abutment wall 78 proximally spaced from plate 80 and extending perpendicularly from side 144 in the direction of a longitudinal axis of the retractable safety penetrating instrument. Operating flange 50 is disposed between plate 80 and abutment wall 78, and the cylindrical body 48 has prongs at the proximal end 52 passing through corresponding slots 145 in plate 80. Coil spring 64 is disposed concentrically around tube 60 and mounted in compression between flange 50 and end wall 62 of hub 36 to bias the penetrating member 32 distally such that flange 50 is biased against plate 80. An annular rim 146 is formed on tube 60 to be disposed in the proximal end 52 of the penetrating member 32, and a stronger, coil retracting spring 85 is disposed concentrically around tube 60 within the proximal end 52 of the penetrating member 32 and is mounted in compression between rim 146 and plate 80 to bias rail 74 and, via abutment with flange 50, the penetrating member 32 in the proximal direction. To simplify assembly of the retracting mechanism 72 and the penetrating member 32, flange 50 can be removably attached, such as by threads or the like, to the cylindrical body 48 at the proximal end 52 of the penetrating member. A locking and releasing mechanism 86 prevents proximal movement of retracting mechanism 72 and includes a latch or locking spring 88 having a substantially flat base 90 secured to a side wall of the hub 36 and terminating proximally in a bend 92 adjacent end wall 62 and an arm 94 joined to bend 92 and extending angularly, distally therefrom in the direction of the longitudinal axis. A finger 96 on a distal end 98 of the arm 94 projects inwardly toward the longitudinal axis and engages plate 80 to hold the plate against front wall 54 of hub 36. Latch 88 has a curved section 100 disposed proximally of finger 96, the curved section 100 curving toward the base 90 to define a clearance, and a releasing or trigger member such as cam 102 is mounted in the clearance to rotate on pin 104. Trigger or leaf spring 106 extends from a distal portion of the cam 102 angularly, proximally in the direction of the longitudinal axis, the cam 102 being positioned by arm 94 such that the trigger 106 is disposed in a rest position proximally of operating flange 50 in the path of movement of the flange. The portal sleeve 34 has proximal end 112 secured to front wall 116 of the housing 38. With the penetrating member unit combined with the portal unit such that the front wall 54 of the hub 36 abuts the end wall 132 of housing 38, junction 46 of the penetrating member 32 is positioned distally of peripheral edge 110 of portal sleeve 34, and the distance from junction 46 to the peripheral edge 110 is the same as the distance from a proximal face of flange 50 to a distal face of abutment wall 78.

According to a method of operation for the retractable safety penetrating instrument 140, the latch 88 is normally in the position shown in FIG. 9 with trigger 106 in the rest position and finger 96 engaging plate 80 such that the retracting mechanism 72 can not move proximally and is, therefore, locked with plate 80 held against front wall 54 of hub 36. Spring 64 is normally in the position shown in FIG. 9 such that the penetrating member 32 is biased distally with flange 50 abutting plate 80 and peripheral edge 110 is proximally spaced from junction 46 as shown in FIG. 9 prior to penetration of tissue T. When the retractable safety penetrating instrument is forced into tissue T as shown in FIG. 10, the penetrating member 32 will move proximally against the distal bias of spring 64 due to the proximal force from tissue contact such that junction 46 will be substantially aligned with peripheral edge 110 of the portal sleeve to present a stable, substantially smooth profile facilitating penetration of tissue T. The proximal face of flange 50 will abut the distal face of abutment wall 78 providing a positive stop limiting proximal movement of the penetrating member 32. During movement past trigger 106, flange 50 urges the trigger clockwise looking at FIG. 10; however, this movement does not disengage the latch 88 from the plate 80 and the trigger returns to the rest position as soon as the flange 50 has moved proximally therepast. Once the distal end of the portal sleeve 34 has entered the anatomical cavity such that force from tissue contact at the distal end of the retractable safety penetrating instrument is removed, the penetrating member 32 will be moved distally due to the distal bias of spring 64, and the distal end 40 of the penetrating member will protrude slightly beyond the peripheral edge 110 of the portal sleeve 34 as shown in FIG. 11. The distance that the penetrating member 32 protrudes from the portal sleeve 34 can be controlled or varied by adjusting the axial position of trigger 106 in the path of movement of flange 50. Once the operating flange 50 engages trigger 106 and pulls the trigger distally, the cam 102 will be rotated counterclockwise looking at FIG. 11 and forced against the latch 88 in a direction outwardly from the longitudinal axis. Accordingly, arm 94 will be moved outwardly in the direction of base 90 to release finger 96 from engagement with plate 80 allowing retracting mechanism 72 to move proximally due to the proximal bias of strong retracting spring 85 overcoming the distal bias of spring 64. The retracting mechanism 72 will carry the penetrating member 32 proximally due to engagement of plate 80 with flange 50, the tube 60 guiding proximal movement of the penetrating member. With the penetrating member 32 moved proximally by the retracting mechanism 72, the sharp tip 42 of the penetrating member is retracted within the distal end 108 of the portal sleeve 34 and the flange 50 is positioned proximally of trigger 106, the trigger 106 having returned to the rest position as shown in FIG. 12. The sharp tip 42 of the penetrating member 32 remains retracted until the penetrating member is reset by being manually moved in the distal direction via knob 58 such that plate 80 abuts front wall 54 of hub 36 and is held by finger 96. Ball detents 39 can be released allowing the penetrating member unit to be removed from the portal unit leaving the portal sleeve 34 in place. The retractable safety penetrating instrument 140 is particularly advantageous in that the retracting mechanism 72, the positive stop and the portal sleeve 34 are of simplified construction enhancing ease of manufacture, assembly and use.

A modification of a retractable safety penetrating instrument according to the present invention is illustrated in FIG. 13 at 150. The retractable safety penetrating instrument 150 is similar to retractable safety penetrating instrument 30 and includes penetrating member 32 having retracting mechanism 72 with cylindrical rail 74 and plate 80 mounted on proximal end 52 of the penetrating member 32. A protrusion or pin 82 on the rail 74 is received within the slot 56 in the penetrating member 32. Retracting spring 85 biases the retracting mechanism 72 and, via abutment of pin 82 with a proximal end of slot 56, the penetrating member 32 in a proximal direction. Locking and releasing mechanism 86 is disposed in hub 36 and is of integral, unitary construction including latch or locking spring 108 having a substantially flat base 90, a proximal bend 92 disposed adjacent end wall 62, an arm 94 extending angularly, distally, from the bend 92 in the direction of a longitudinal axis of the retractable safety penetrating instrument and a bent finger 96 at a distal end 98 of the arm 94 engaging the plate 80 and preventing proximal movement of the retracting mechanism 72 due to the proximal bias of strong retracting spring 85. Arm 94 is bifurcated to form a releasing or trigger member including trigger or leaf 106 extending angularly, proximally in the direction of the longitudinal axis and spring biased to a rest position shown in FIG. 13, with the operating flange 50 of the penetrating member 32 being positioned distally of the trigger 106 in the rest position due to the distal bias of spring 64. The portal sleeve 34 has a proximal end 112 secured to front wall 116 of the housing 38. With the penetrating member unit combined with the portal unit such that the front wall 54 of the hub 36 abuts the end wall 132 of the housing 38, junction 46 of the penetrating member 32 is positioned distally of the peripheral edge 110 of the portal sleeve 34, and the distance from junction 46 to the peripheral edge 110 is the same as the distance from the distal end 136 of the slot 56 to the pin 82, the pin 82 serving as a positive stop limiting proximal movement of the penetrating member.

According to a method of operation for the retractable safety penetrating instrument 150, the latch 88 is normally in the position shown in FIG. 13 with trigger 106 in the rest position and finger 96 engaging plate 80 such that the retracting mechanism 72 cannot move proximally and is, therefore, locked with plate 80 held against front wall 54 of hub 36. Spring 64 is normally in the position shown in FIG. 13 such that the penetrating member 32 is biased distally with the peripheral edge 110 of the portal sleeve 34 proximally spaced from junction 46 as shown in FIG. 13 prior to penetration of tissue T. When the retractable safety penetrating instrument 150 is forced into the tissue T, the penetrating member 32 will move proximally against the distal bias of spring 64 such that junction 46 will be substantially aligned with the peripheral edge 110 of the portal sleeve 34 to present a substantially smooth profile facilitating penetration of tissue as shown in FIG. 10 for retractable safety penetrating instrument 140. The distal end 136 of the slot 56 will abut the pin 82 providing a positive stop limiting proximal movement of the penetrating member 32; and, in this position, the flange 50 will be positioned proximally of the trigger 106. As the flange 50 moves proximally past the trigger 106, finger 96 remains engaged with the plate 80 preventing proximal movement of the retracting mechanism 72. Upon penetration of the distal end of the portal sleeve 34 into the anatomical cavity, the penetrating member 32 will be moved distally due to the distal bias of spring 64 and the distal end 40 of the penetrating member 32 will protrude slightly beyond the peripheral edge 110 of the portal sleeve 34 as shown in FIG. 11 for retractable safety penetrating instrument 140. However, once the operating flange 50 engages trigger 106 and pulls the trigger distally, the distal end 98 of the arm 94 will be bent angularly, outwardly toward base 90 releasing the finger 96 from engagement with the plate 80. The retracting mechanism 72 is then free to move proximally due to the proximal bias of strong retracting spring 85 overcoming the distal bias of spring 64, and the retracting mechanism 72 carries the penetrating member 32 proximally such that the sharp tip 42 at the distal end 40 of the penetrating member 32 is protected within the distal end 108 of the portal sleeve 34 as shown in FIG. 12 for retractable safety penetrating instrument 140. With the retracting mechanism 72 and penetrating member 32 biased proximally, the flange 50 is positioned proximally of trigger 106, the trigger 106 returning automatically to the rest position. The sharp tip 42 of the penetrating member 32 remains retracted until the retractable safety penetrating instrument is reset by manually moving the penetrating member 32 in the distal direction via knob 58 to position plate 80 against front wall 54 of hub 36 and held by finger 96.

A further modification of a retractable safety penetrating instrument according to the present invention is shown in FIG. 14 at 160. The safety penetrating instrument 160 includes penetrating member 32, portal sleeve 34 concentrically disposed around penetrating member 32, a middle member 162 disposed between penetrating member 32 and portal sleeve 34, hub 36 mounting penetrating member 32 and middle member 162 and housing 38 mounting portal sleeve 34. Penetrating member 32 has a distal end 40 with conical end surface 44 tapering to sharp tip 42 and a proximal end 52 terminating at operating flange 50 disposed in hub 36. Conical end surface 44 is joined to a cylindrical neck 166, and the cylindrical body 48 extends proximally from neck 166 to flange 50. A thread 165 is disposed along conical end surface 44 from junction 46 to tip 42. Cylindrical body 48 has a forward, enlarged diameter section 168 joined to neck 166, a rearward, enlarged diameter section 170 joined to flange 50 and an intermediate section 172 disposed between forward and rearward sections 168 and 170 and having an outer diameter smaller than the outer diameters of the forward and rearward sections 168 and 170. Forward section 168 has an outer diameter smaller than the outer diameter of neck 166, and a proximal end of the forward section 168 is received in a distal end 174 of middle member 162 such that the neck 166 is spaced distally from the distal end 174 of the middle member 162, the distal end 174 of the middle member 162 being disposed within the portal sleeve 34 to serve as a positive stop limiting proximal movement of the penetrating member 32. The distal end 174 of middle member 162 has an outer diameter the same as the outer diameter of neck 166. Middle member 162 includes a cylindrical body 176 having an outer diameter smaller than the outer diameter of distal end 174 for concentrically receiving the intermediate section 172 of penetrating member 32, the inner diameter of the cylindrical body 176 of the middle member 162 being substantially the same as the outer diameter of the intermediate section 172 of the penetrating member 32. The cylindrical body 176 of middle member 162 terminates at plate 80 at a proximal end 178 disposed in hub 36. Tube 60 extends from end wall 62 of hub 36 into proximal end 52 of penetrating member 32, and spring 64 is disposed around tube 60. Spring 64 is mounted in compression between flange 50 and end wall 62 such that the penetrating member 32 is biased distally with rearward section 170 biased against plate 80. Front wall 54 of hub 36 has an annular skirt 180 extending distally therefrom and terminating at an end face 182 having an opening therein for receiving the cylindrical body 176 of middle member 162. Strong retracting spring 85 is disposed around the cylindrical body 176 of middle member 162 within skirt 180, the retracting spring 85 being mounted in compression between end face 182 and plate 80 to bias the middle member 162 and, via abutment with rearward section 170, the penetrating member 32 in the proximal direction. Locking and releasing mechanism 86 mounted in hub 36 prevents proximal movement of middle member 162 and includes a latch having locking springs 88, each locking spring 88 including a substantially flat base 90 secured to a side wall of hub 36, a proximal bend 92 and an arm 94 extending angularly, distally from bend 92 in the direction of a longitudinal axis of the safety penetrating instrument and having a distal portion 182 bent angularly, distally in a direction outwardly from the longitudinal axis toward plate 80. Fingers 96 on the distal portions 182 of arms 94 engage plate 80 and hold the plate against front wall 54 of hub 36. A releasing or trigger member includes trigger or leaves 106 extending from distal portions 182 of the arms 94 and curving proximally toward bases 90 and inwardly toward the longitudinal axis, the triggers 106 being spring biased to a rest position shown in FIG. 14 wherein the triggers are disposed in the path of movement of the operating flange 50. Portal sleeve 34 has a distal end 108 with peripheral edge 110 and a proximal end 112 with flange 114 disposed in housing 38, flange 114 being biased distally by springs 122. With skirt 180 extending into housing 38 via an opening in the end wall 132, springs 64 and 122 bias the penetrating member 32 and the portal sleeve 34, respectively, distally such that the junction 46 is substantially aligned with the peripheral edge 110 of the portal sleeve 34 and a proximal end of neck 166 is disposed in the portal sleeve 34. During penetration of tissue of a cavity wall, the penetrating member 32 is inserted in tissue with a relatively slow, rotational motion due to thread 165 on conical end surface 40, and the relative positions of the distal ends of the penetrating member 32 and the portal sleeve 34 will be as shown in FIGS. 5–8. Insertion of the penetrating member in tissue with a rotational motion allows penetration through a cavity wall to be accomplished with greater control through gradual advancement of the penetrating member and is particularly advantageous when entering very small or narrow anatomical cavities. When the penetrating member 32 is moved proximally due to the proximal force from tissue contact at the distal end 40, flange 50 will move proximally past the triggers 106 while fingers 96 remain engaged with plate 80, abutment of the proximal end of neck 166 with the distal end 174 of the middle member serving as a positive stop limiting proximal movement of the penetrating member 32. The portal sleeve 34 will move proximally against the distal bias of springs 122, and the distance that the portal sleeve moves proximally is the same as the distance from the proximal end of neck 166 to the distal end 174 of the middle member 162 such that the junction 46 and the peripheral edge 110 are stable and aligned during penetration through the tissue. Upon penetration of the distal end of the portal sleeve 34 into the cavity, penetrating member 32 will be moved distally due to the distal bias of spring 64 and operating flange 50 will engage triggers 106 pulling the triggers distally while the distal portions 182 of arms 94 will be bent angularly in a direction outwardly from the longitudinal axis such that the fingers 96 will be disengaged from plate 80. The middle member 162 is then free to move proximally due to the proximal bias of strong retracting spring 85 overriding the distal bias of spring 64 and engagement of plate 80 with the rearward section 170 of the penetrating member 32 causes the penetrating member to be carried proximally with the middle member 162. With the penetrating member 32 and middle member 162 biased proximally, the sharp tip 42 of the penetrating member 32 will be retracted within the distal end 108 of the portal sleeve 34 and protected from inadvertent contact with tissue in or forming the anatomical cavity. The sharp tip 42 will remain retracted until the retractable safety penetrating instrument is reset by moving the penetrating member 32 distally via knob 58.

As shown in FIG. 14, the distal end 40 of the penetrating member 32 can be formed to be interchangeable with cylindrical body 48. Forward section 168 of cylindrical body 48 has an internally threaded socket 184 for receiving an externally threaded shaft 186 extending from neck 166; and, accordingly, various configurations of solid and hollow penetrating member distal tips can be mounted on cylindrical body 48 such that the retractable safety penetrating instrument is suited for universal use in various least invasive procedures.

Another modification of a retractable safety penetrating instrument according to the present invention is illustrated in FIG. 15 at 200. The retractable safety penetrating instrument 200 includes penetrating member 32, portal sleeve 34 concentrically disposed around penetrating member 32, middle member 162 disposed between penetrating member 32 and portal sleeve 34, hub 36 mounting penetrating member 32 and housing 38 mounting portal sleeve 34. The penetrating member 32 has a distal end 40 terminating at sharp tip 42 defined by three, equally spaced end surfaces or facets 44 having straight edges 151 terminating proximally at junction 46 joining the facets 44 to a cylindrical neck 166. Cylindrical body 48 extends proximally from neck 166 to proximal end 52 terminating at operating flange 50 disposed in hub 36, the cylindrical body 48 having an outer diameter smaller than the outer diameter of neck 166. Middle member 162 is concentrically disposed around penetrating member 32 and has a distal end 174 disposed within the portal sleeve 34 proximally spaced from peripheral edge 110 and a proximal end 178 secured to front wall 54 of hub 36, the outer diameter of the middle member 162 being the same as the outer diameter of neck 166. Tube 60 extends from end wall 62 of hub 36 into proximal end 52 of the penetrating member 32, and spring 64 is disposed around the tube 60. Spring 64 is mounted in compression between flange 50 and end wall 62 to bias the penetrating member 32 in a distal direction such that flange 50 is biased against plate 80. A retracting mechanism 72 is mounted on proximal end 52 of the penetrating member 32 and includes plate 80 disposed distally of flange 50, an annular skirt 202 extending distally from plate 80 toward front wall 54 of the hub 36 and strong retracting spring 85 disposed around the proximal end 52 of the penetrating member 32 within the skirt 202. Retracting spring 85 is mounted in compression between front wall 54 of hub 36 and plate 80 to bias the penetrating member 32 in a proximal direction. Locking and releasing mechanism 86 disposed in hub 36 prevents proximal movement of the penetrating member 32 and includes a latch having locking bars 204 biased by locking springs 88 into engagement with plate 80. Locking bars 204 are pivotably secured at 206 to end wall 62 of hub 36 on diametrically opposite sides of tube 60 and extend angularly, distally toward a longitudinal axis of the retractable safety penetrating instrument, the locking bars 204 terminating distally at fingers 96 angled from bars 204 in a direction outwardly from the longitudinal axis. Locking springs 88 bias the locking bars 204 in a direction inwardly toward the longitudinal axis such that the fingers 96 engage plate 80 to prevent proximal movement of the penetrating member 32. Each locking spring 88 includes a base 90 secured to a side wall of the hub 36 and extending distally to a bend 92 and an arm 94 extending angularly, proximally from bend 92 in the direction of the longitudinal axis. Arms 94 are bifurcated to define webs 208 connecting springs 88 with fingers 96 to position the fingers in engagement with plate 80 and releasing or trigger members including triggers or leaves 106 spring biased to be disposed in the path of movement of flange 50. Portal sleeve 34 includes distal end 108 terminating at peripheral edge 110 and proximal end 112 secured to front wall 116 of housing 38.

According to a method of operation for retractable safety penetrating instrument 200, the locking springs 88 are normally in the position shown in FIG. 15 with arms 94 biasing fingers 96 into engagement with plate 80 via webs 208 such that the penetrating member 32 cannot move proximally. Spring 64 is normally in the position shown in FIG. 15 such that the penetrating member 32 is biased distally with flange 50 biased against plate 80. With the penetrating member 32 biased distally, junction 46 is positioned distally of the peripheral edge 110 of the portal sleeve 34 while a proximal end of neck 166 is disposed within the portal sleeve 34. The distance from junction 46 to the peripheral edge 110 is the same as the distance from the proximal end of the neck 166 to the distal end 178 of the middle member 162 when the penetrating member 32 is distally biased by spring 64 prior to penetration of tissue of an anatomical cavity wall. When the safety penetrating instrument 200 is forced into the tissue, the penetrating member 32 will move proximally against the distal bias of spring 64 due to the proximal force from tissue contact at the distal end of the retractable safety penetrating instrument such that junction 46 will be substantially aligned with the peripheral edge 110 of the portal sleeve 34 presenting a substantially smooth profile during penetration of tissue. The proximal end of the neck 166 will abut the distal end 178 of the middle member 162 serving as a positive stop limiting proximal movement of the penetrating member 32. Flange 50 will move proximally past the triggers 106 while the fingers 96 remain engaged with plate 80. Upon penetration of the distal end 108 of the portal sleeve 34 into the anatomical cavity, the penetrating member 32 will be moved distally due to the distal bias of spring 64 and junction 46 will move distally of peripheral edge 110 a short distance. As the penetrating member 32 moves distally, flange 50 engages the triggers 106 and pulls the triggers distally forcing arms 94 of the locking springs 88 outwardly toward the bases 90 such that the fingers 96 are pulled by webs 208 in a direction outwardly from the longitudinal axis and out of engagement with plate 80. With fingers 96 disengaged from plate 80, the retracting mechanism 72 and, therefore, the penetrating member 32, will be free to move proximally due to the proximal bias of strong retracting spring 85 overriding the distal bias of spring 64. With the penetrating member 32 proximally biased, the locking bars 204 will be disposed along skirt 202, and the sharp tip 42 of the penetrating member 32 will be disposed within the portal sleeve 34.

Another modification of a retractable safety penetrating instrument according to the present invention is shown in FIG. 16 at 210. The retractable safety penetrating instrument 210 includes penetrating member 32, portal sleeve 34 concentrically disposed around penetrating member 32, a safety probe 212 disposed within penetrating member 32, hub 36 mounting penetrating member 32 and safety probe 212 and housing 38 mounting portal sleeve 34. The penetrating member 32 is cannulated and has an open distal end 40 with an end surface 164 disposed at an acute angle with a longitudinal axis of the retractable safety penetrating instrument and a proximal end 52 disposed in hub 36. End surface 164 tapers distally to sharp tip 42 and is joined proximally to cylindrical body 48 at junction 46, the cylindrical body 48 extending proximally from junction 46 to shoulder 211 at the proximal end 52 of the penetrating member 32. Retracting mechanism 72 is mounted on proximal end 52 of the penetrating member 32 and includes plate 80 disposed distally of shoulder 211, an annular skirt 202 extending distally from plate 80 toward front wall 54 of the hub 36 and strong retracting spring 85 disposed around the proximal end 52 the penetrating member within skirt 202. The retracting spring 85 is mounted in compression between the front wall 54 of the hub 36 and the plate 80 such that the penetrating member 32 is biased in a proximal direction. The safety probe 212 includes a blunt distal end 214 with an angled end surface 215 and a hollow proximal end 216 terminating at flange 50 within hub 36, the proximal end 216 passing through an opening in plate 80. Tube 60 extends distally from end wall 62 of the hub 36 into the proximal end 216 of the safety probe 212, and a spring 64 is disposed around tube 60. Spring 64 is mounted in compression between flange 50 and end wall 62 such that the safety probe 212 is biased in a distal direction with flange 50 biased against shoulder 211. Locking and releasing mechanism 86 disposed in hub 36 prevents proximal movement of the penetrating member 32 and includes a latch having locking bars 204 biased by locking springs 88 into engagement with plate 80. Locking bars 204 are pivotably secured at 206 to end wall 62 of hub 36 on diametrically opposite sides of tube 60 and extend angularly, distally toward a longitudinal axis of the retractable safety penetrating instrument, the locking bars 204 terminating distally in fingers 96 angled from locking bars 204 in a direction outwardly from the longitudinal axis. Locking springs 88 bias the locking bars 204 in a direction inwardly toward the longitudinal axis such that the fingers 96 engage plate 80 to prevent proximal movement of the penetrating member 32. Each locking spring 88 includes a base 90 secured to a side wall of the hub 36 and extending distally to a bend 92 and an arm 94 extending angularly, proximally from bend 92 in the direction of the longitudinal axis. Arms 94 are bifurcated to define webs 208 connecting springs 88 with fingers 96 to position the fingers in engagement with plate 80 and releasing or trigger members including triggers or leaves 106 spring biased to be disposed in the path of movement of flange 50 of safety probe 212. Protrusions or bumps 102 extend from locking bars 204 in the direction of the longitudinal axis and are positioned proximally of triggers 106 to serve as a positive stop limiting proximal movement of the safety probe 212. Portal sleeve 34 includes distal end 108 terminating at peripheral edge 110 and proximal end 112 secured to front wall 116 of housing 38.

According to a method of operation for retractable safety penetrating instrument 210, the locking springs 88 are normally in the position shown in FIG. 16 with fingers 96 biased into engagement with plate 80 such that the penetrating member 32 cannot move proximally. Spring 64 is normally in the position shown in FIG. 16 such that the safety probe 212 is biased distally with flange 50 biased against shoulder 211 such that the distal end 214 of the safety probe 212 protrudes beyond and protects the sharp tip 42 of the penetrating member 32, with the angled end surface 215 of the safety probe disposed substantially parallel with the end surface 164 of the penetrating member 32. The junction 46 of the penetrating member 32 is substantially aligned with the peripheral edge 110 of the portal sleeve presenting a substantially smooth profile for tissue penetration. When the safety penetrating instrument 210 is forced into the tissue T, the safety probe 212 will move proximally against the distal bias of spring 64 due to the proximal force from tissue contact at the distal end of the retractable safety penetrating instrument such that the angled end surface 215 of the safety probe 212 will be substantially aligned with the end surface 164 of the penetrating member 32 presenting a substantially solid configuration for penetration through tissue T as shown in FIG. 17. With end surface 215 aligned with end surface 164, flange 50 will be engaged with protrusions 102 and the safety probe 212 will be prevented from further proximal movement. Flange 50 will have moved proximally past the triggers 106; however, the fingers 96 will remain engaged with plate 80. Upon penetration of the distal end 108 of the portal sleeve 34 into the anatomical cavity, the safety probe 212 will move distally due to the distal bias of spring 64, and end surface 215 will move distally of end surface 164 a slight distance as shown in FIG. 18. As the safety probe 212 moves distally, flange 50 engages triggers 106 and pulls the triggers distally forcing arms 94 of the locking springs 88 outwardly toward the bases 90 such that the fingers 96 are pulled via the webs 208 in a direction outwardly from the longitudinal axis and out of engagement with plate 80. With fingers 96 disengaged from plate 80, the penetrating member 32 is free to move proximally due to the proximal bias of strong retracting spring 85 overriding the distal bias of spring 64, and the safety probe 212 will be moved proximally along with the penetrating member 32 due to abutment of shoulder 211 with flange 50 as shown in FIG. 19. With the penetrating member 32 and the safety probe 212 proximally biased, the locking bars 204 will be disposed along skirt 202, and the sharp tip 42 of the penetrating member 32 will be protected within the portal sleeve 34. It will be appreciated that the distance that the end surface 215 is allowed to protrude beyond the end surface 164 prior to retraction can be varied or controlled by adjusting the axial location of the triggers 106 within the path of movement of flange 50.

Another modification of a safety penetrating instrument according to the present invention is shown in FIG. 20 at 220. The safety penetrating instrument 220 is best suited for penetrating relatively thin anatomical cavity walls or easily penetrable tissue and includes penetrating member 32 having a cylindrical body 48 terminating proximally at plate 80 having an aperture therein receiving tube 60 in the proximal end 52 of the penetrating member 32. Tube 60 extends from an end wall 62 of a hub or end cap 36 to an annular rim 146 disposed within the proximal end 52 of the penetrating member 32. A retracting spring 85 is disposed within the proximal end 52 of the penetrating member 32 concentrically around tube 60 and is mounted in compression between the rim 146 and the plate 80 to bias the penetrating member 32 in a proximal direction. A locking and releasing mechanism 86 disposed in housing 38 prevents proximal movement of penetrating member 32 and includes a latch or locking spring 88 mounted in the lumen of tube 60 and having a base 90 secured to a wall of the tube 60, a proximal bend 92 extending through a longitudinal aperture 224 in the tube 60 in a direction angularly, distally, outwardly from a longitudinal axis of the safety penetrating instrument and an arm 94 extending distally from bend 92 parallel with the longitudinal axis externally of tube 60. A finger 96 on a distal end 98 of arm 94 engages the plate 80 and prevents proximal movement of the penetrating member 32, and a bump or curve 223 on arm 94 projects in a direction outwardly from the longitudinal axis. Portal sleeve 34 includes a distal end 108 and a proximal end 112 with flange 114 disposed in housing 38. Tube 60 extends through an opening in a rear wall 132 of the housing 38 such that the penetrating member 32 extends through the portal sleeve 34 with plate 80 disposed in housing 38 proximally of intermediate wall 118. A spring 122 is disposed concentrically around the proximal end 52 of the penetrating member 32 and is mounted in compression between flange 114 and intermediate wall 118 to bias the portal sleeve 34 in a distal direction. With end cap 36 abutting rear wall 132 of housing 38 and portal sleeve 34 biased distally by spring 64, peripheral edge 110 is substantially aligned with junction 46. A releasing or trigger member includes cam 102 rotatably mounted in housing 38 on a pin 104 extending transverse to the longitudinal axis and having ends secured to walls of housing 38, the pin 104 passing through cam 102 off-center with a longitudinal axis of the cam. As shown in FIG. 24, a spring 225 is disposed around pin 104 and is secured, respectively, to housing 38 and cam 102, the spring 225 being wound in torsion to torsionally bias cam 102 to a rest position shown in FIG. 20. Cam 102 is positioned laterally adjacent bump 223, and a trigger 106 extends from a proximal portion of cam 102 in a direction radially outwardly from the longitudinal axis of the retractable safety penetrating instrument. An operating member including operating or cocking arm 226 extends proximally from flange 114 through an opening in intermediate wall 118 and terminates in a hook 228 disposed distally of trigger 106.

In a method of operation for the retractable safety penetrating instrument 220, the locking spring 88 is normally in the position shown in FIG. 20 with cam 102 and trigger 106 in a rest position and finger 96 of the locking spring 88 engaging plate 80 such that the penetrating member 32 cannot move proximally and is, therefore, locked. Spring 122 is normally in the position shown in FIG. 20 such that the portal sleeve 34 is biased distally with peripheral edge 110 substantially aligned with junction 46 prior to penetration of tissue T of an anatomical cavity wall. When tissue T is to be penetrated, the end cap 36 and housing 38 are gripped in one hand and the safety penetrating instrument is forced into the tissue T as shown in FIG. 21. The portal sleeve 34 will move proximally against the distal bias of spring 122 due to the proximal force from tissue contact such that peripheral edge 110 will be positioned proximally of junction 46, and the portal sleeve 34 will follow the penetrating member 32 through the tissue as shown in FIG. 21. Portal sleeve 34 will move proximally until spring 122 is compressed between flange 114 and intermediate wall 118 serving as a positive stop limiting proximal movement of the portal sleeve, and the hook 228 on the operating arm 226 will move proximally past the trigger 106 as shown in FIG. 21. As the operating arm 226 moves proximally past the trigger 106, the finger 96 remains engaged with the plate 80 preventing proximal movement of the penetrating member 32. Once the distal end 108 of the portal sleeve 34 has entered the anatomical cavity, the portal sleeve 34 will be moved distally due to the distal bias of spring 122 such that the peripheral edge 110 approaches junction 46. As the portal sleeve 34 moves distally, hook 228 of operating arm 226 engages trigger 106 and pulls the trigger distally causing the cam 102 to rotate clockwise as shown in FIG. 22. Accordingly, the cam 102 is forced against bump 223 moving arm 94 into aperture 224 and causing the finger 96 to be released from plate 80 as shown in FIG. 22. Once released, the locking spring 88 will enter the aperture 224 in tube 60 and the penetrating member 32 will be moved proximally due to the proximal bias of retracting spring 85 such that the sharp tip 42 of the penetrating member 32 is disposed within the distal end 108 of the portal sleeve 34 as shown in FIG. 23. With the penetrating member 32 biased proximally, the hook 228 on the operating arm 226 is disposed distally of the trigger 106. The safety penetrating instrument 220 can be reset for further use by moving the penetrating member 32 distally via knob 58 as previously described.

Modifications of a retracting mechanism and locking and releasing mechanism for the retractable safety penetrating instrument of the present invention are shown in FIG. 25 at 240 and 241, respectively. Retracting mechanism 240 includes plate 80, cylindrical rail 74, retracting spring 85 mounted on rail 74 and a pin or protrusion 82 projecting from the periphery of the rail 74 such that flange 50 of penetrating member 32 is disposed between plate 80 and pin 82. Flange 50 is biased distally against plate 80 by spring 64 with the protrusion 82 serving as a positive stop limiting proximal movement of the penetrating member 32. A ledge 242 projects perpendicularly from plate 80 in a proximal direction parallel with a longitudinal axis of the retractable safety penetrating instrument, and a slot 244 is formed in the ledge 242 to extend parallel with the longitudinal axis. As shown in FIG. 25 and 26, locking and releasing mechanism 241 includes a latch or locking spring 88 having a substantially flat base 90 secured to a side wall of hub 36, a distal bend 92 adjacent the front wall 54 of the hub 36 and an arm 94 extending proximally from the bend 92 substantially parallel with the longitudinal axis. A curved finger 96 at a proximal end of the arm 94 engages the ledge 242 and prevents proximal movement of the retracting mechanism 240. Arm 94 is bifurcated to form a release or trigger member including trigger or leaf 106 extending toward the longitudinal axis with a distal curvature, the trigger 106 extending through the slot 244 in the ledge 242 to be spring biased in the path of movement of flange 50. In operation, when flange 50 moves proximally against the distal bias of spring 64 due to a proximal force from tissue contact at the distal end of the retractable safety penetrating instrument, the flange 50 moves trigger 106 proximally in the slot 244 allowing the flange to move therepast while finger 96 remains engaged with ledge 242, and the pin 82 serves as a positive stop limiting proximal movement of the penetrating member 32. Once the force from tissue contact is removed from the distal end of the retractable safety penetrating instrument upon penetration through tissue forming a cavity wall, the penetrating member 32 is moved distally due to the distal bias of spring 64 causing flange 50 to engage and bend the trigger 106 distally such that the arm 94 is bent angularly in a direction outwardly from the longitudinal axis and toward the base 90 with finger 96 being disengaged from the ledge 242. The retracting mechanism 240 is then free to move proximally due to the proximal bias of strong retracting spring 85 overcoming the distal bias of spring 64, and the penetrating member 32 will be moved proximally with the retracting mechanism 240 such that the sharp tip at the distal end of the penetrating member 32 will be protected within the portal sleeve 34.

Most complications from introduction of a portal sleeve into an anatomical cavity with a trocar or other penetrating member result from the surgeon not using a smooth, continuous movement in forcing the penetrating instrument through the cavity wall. That is, when the penetrating movement is jerky or not smoothly continuous, entry into the cavity is frequently accomplished with too much force resulting in undesirable contact with tissue or organ structures in the cavity even if safety penetrating instruments are used; and, additionally, a jerky, discontinuous movement creates uneven tissue tearing rather than the minimal incision sought with endoscopic or least invasive surgery. One of the advantages of the present invention is that use of the retractable safety penetrating instrument encourages a smooth, continuous penetrating movement by the surgeon in that should the surgeon use a jerky penetrating movement the penetrating member will retract within the portal sleeve due to the proximal movement of the retractable safety penetrating instrument by the surgeon. That is, when the surgeon moves the retractable safety penetrating instrument proximally or rearwardly, as occurs when the surgeon is hesitant or unsure, the operating member will move distally to trigger retraction of the penetrating member. Thus, the retractable safety penetrating instrument not only provides safe penetration of an anatomical cavity but also assures proper use of the penetrating instrument to minimize trauma.

The retractable safety penetrating instrument of the present invention includes a portal sleeve receiving a penetrating member having a sharp distal tip protruding beyond a distal end of the portal sleeve for penetrating tissue and retractable to a protected position via a trigger responsive to movement of the retractable safety penetrating instrument distally upon entering a body cavity. The penetrating member and portal sleeve can both be biased distally, the penetrating member can be biased distally with the portal sleeve being fixed, or the penetrating member can be fixed with the portal sleeve biased distally. The penetrating member and the portal sleeve can be biased by springs or other suitable devices for applying a biasing force, and biasing devices can be mounted within, around or laterally of the penetrating member and the portal sleeve. The retracting spring for moving the penetrating member proximally can be mounted externally of, concentrically around or within the penetrating member, and various rail configurations can be employed to mount the retracting spring externally of the penetrating member. A variety of positive stop configurations can be utilized to limit proximal movement of the penetrating member during penetration of tissue, and the positive stops can be provided at the distal end or the proximal end of the retractable safety penetrating instrument. The locking mechanism for preventing movement of the penetrating member proximally can include a variety of latches or springs, and the release mechanism can include cams, spring-like members or any suitable means for releasing the locking mechanism by an action to move the latch or lock member out of the path of movement of the penetrating member or a rail movable therewith, such as in camming, spring, bending or buckling type actions and the like. The locking and releasing mechanism can be of multi-part or integral, unitary construction and can be disposed within the hub or the housing. The penetrating member must be securely held or locked in position prior to triggering of the retraction mechanism; and, thus, the latch members are preferably secured to the housing and can include multi-part or unitary flexible spring members operated by leaves or cams as well as pivoted rigid members secured to the housing. The operating member for engaging the trigger can be provided on the penetrating member, the portal sleeve, a middle member disposed between the penetrating member and the portal sleeve or an inner member disposed within the penetrating member. Where the operating member includes a tube slidably disposed between the penetrating member and the portal sleeve, such as middle member 162 in the embodiment of FIG. 14, the tube can extend beyond the distal end of the portal sleeve to surround the sharp tip of the penetrating member prior to penetration of a cavity wall. In this manner the middle member protects the sharp tip prior to use while also causing retraction of the penetrating member after penetration into the cavity. The sharp distal end of the penetrating member can have various solid or hollow geometrical configurations, and the distal end of the penetrating member can be interchangeably mounted on the cylindrical body of the penetrating member.

Having described preferred and alternative embodiments of a new and improved retractable safety penetrating instrument for portal sleeve introduction, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A retractable safety penetrating instrument for forming a portal communicating with a cavity in the body to allow passage of instruments for performing least invasive medical procedures comprising a hollow portal sleeve for providing a passage through a cavity wall and having a distal end for positioning in the body cavity, a proximal end for positioning externally of the body cavity and a lumen extending between said distal and proximal ends;

a penetrating member disposed in said lumen of said sleeve and having a distal end for penetrating the cavity wall and a hollow proximal end;

a hub mounting said proximal end of said penetrating member and having proximal wall;

retracting means for moving said penetrating member proximally relative to said sleeve from an extended position where said penetrating member distal end protrudes beyond said sleeve distal end to a retracted position to prevent contact of said penetrating member distal end with tissue, said retracting means including means for biasing said penetrating member in a proximal direction;

a guide tube secured to said hub and extending from said hub proximal wall into said penetrating member proximal end for guiding proximal movement of said penetrating member therealong; and trigger means for automatically actuating said retracting means to move said penetrating member to said retracted position in response to movement of said retractable safety penetrating instrument distally upon said sleeve distal end entering the body cavity whereby said distal end of said penetrating member is protected from inadvertent contact with tissue in the body cavity.

2. A retractable safety penetrating instrument as recited in claim 1 further including means engageable with said retracting means for preventing movement of said penetrating member to said retracted position and said trigger means includes means for automatically disengaging said movement preventing means.

3. A retractable safety penetrating instrument for forming a portal communicating with a cavity in the body to allow passage of instruments for performing least invasive medical procedures comprising a hollow portal sleeve for providing a passage through a cavity wall and having a distal end for positioning in the body cavity, a proximal end for positioning externally of the body cavity and a lumen extending between said distal and proximal ends;

a penetrating member disposed in said lumen of said sleeve and having a distal end for penetrating the cavity wall and a hollow proximal end;

a hub mounting said proximal end of said penetrating member, said hub including cylindrical member means extending into said penetrating member proximal end for guiding proximal movement of said penetrating member;

retracting means for moving said penetrating member proximally relative to said sleeve from an extended position where said penetrating member distal end protrudes beyond said sleeve distal end to a retracted position to prevent contact of said penetrating member distal end with tissue, said retracting means including means for biasing said penetrating member in a proximal direction, said biasing means including a spring disposed within said penetrating member proximal end concentrically around said cylindrical member means; and trigger means for automatically actuating said retracting means to move said penetrating member to said retracted position in response to movement of said retractable safety penetrating instrument distally upon said sleeve distal end entering the body cavity whereby said distal end of said penetrating member is protected from inadvertent contact with tissue in the body cavity.

4. A retractable safety penetrating instrument as recited in claim 3 further including a rim on said cylindrical member means disposed within said proximal end of said penetrating member and a shoulder on said proximal end of said penetrating member, said spring being mounted in compression between said rim and said shoulder.

5. A retractable safety penetrating instrument as recited in claim 3 further including a rim on said cylindrical member means disposed within said proximal end of said penetrating member and a plate extending into said proximal end of said penetrating member, said spring being mounted in compression between said rim and said plate.

6. A retractable safety penetrating instrument as recited in claim 1 wherein said biasing means is disposed within said hub externally of said penetrating member proximal end.

7. A retractable safety penetrating instrument as recited in claim 6 wherein said biasing means includes a spring disposed concentrically around said penetrating member.

8. A retractable safety penetrating instrument as recited in claim 7 further including an abutment wall mounted on said proximal end of said penetrating member and having an aperture allowing passage therethrough of said proximal end of said penetrating member, and an annular skirt disposed concentrically around said proximal end of said penetrating member and extending from said abutment wall, said spring being disposed concentrically around said penetrating member proximal end within said skirt and maintained in compression between said hub and said abutment wall.

9. A retractable safety penetrating instrument as recited in claim 6 further including a middle member disposed between said penetrating member and said portal sleeve and having a proximal end disposed in said hub and a distal end disposed in said portal sleeve and wherein said biasing means includes a spring disposed concentrically around said middle member.

10. A retractable safety penetrating instrument as recited in claim 9 further including a flange on said proximal end of said penetrating member, a plate on said proximal end of said middle member engageable with said flange and an annular skirt extending from said hub concentrically around said middle member and terminating at a shoulder, and wherein said spring is mounted in compression between said shoulder and said plate.

11. A retractable safety penetrating instrument for forming a portal communicating with a cavity in the body to allow passage of instruments for performing least invasive medical procedures comprising a hollow portal sleeve for providing a passage through a cavity wall and having a distal end for positioning in the body cavity, a proximal end for positioning externally of the body cavity and a lumen extending between said distal and proximal ends, said distal end of said portal sleeve including a peripheral edge;

a penetrating member disposed in said lumen of said sleeve and having a distal end for penetrating the cavity wall and a proximal end, said distal end of said penetrating member including an end surface tapering to a sharp tip and a cylindrical body joined to said end surface at a junction;

a hub mounting said proximal end of said penetrating member;

means for biasing said penetrating member distally in said lumen of said sleeve to an extended position where said distal end of said penetrating member is disposed distally of said sleeve distal end and for allowing proximal movement of said penetrating member relative to said sleeve against said distal bias in response to a proximal force from tissue contact at said distal end of said penetrating member during penetration of the cavity wall;

retracting means for automatically moving said penetrating member proximally relative to said sleeve to a retracted position to prevent contact of said distal end of said penetrating member with tissue in response to movement of said penetrating member distally by said distal bias upon removal of the proximal force from tissue contact upon entry into the anatomical cavity; and a stop disposed at said proximal end of said penetrating member for limiting proximal movement of said penetrating member against said distal bias, said junction being aligned with said peripheral edge when said penetrating member moves proximally against said distal bias, as limited by said stop, in response to a proximal force from tissue contact at said distal end of said penetrating member to present a substantially smooth profile during penetration of the cavity wall.

12. A retractable safety penetrating instrument as recited in claim 11 wherein said penetrating member includes a flange on said penetrating member proximal end disposed in said hub and wherein said distal biasing means includes a spring mounted in compression between said flange and said hub.

13. A retractable safety penetrating instrument as recited in claim 1 wherein said hollow proximal end carries a flange and further including means for mounting said penetrating member in said lumen of said sleeve for allowing proximal movement of said penetrating member relative to said sleeve during penetration of the cavity wall, said mounting means including a spring disposed concentrically around said tube and mounted in compression between said flange and said hub for biasing said penetrating member in a distal direction and for allowing proximal movement of said penetrating member against said distal bias in response to a proximal force from tissue contact at said distal end of said penetrating member during penetration, said retracting means retracting said penetrating member relative to said sleeve in response to distal movement of said penetrating member by said distal bias upon removal of the proximal force from tissue contact.

14. A retractable safety penetrating instrument as recited in claim 11 and further including means for permitting said portal sleeve to move proximally in response to a proximal force from tissue contact at said distal end of said portal sleeve during penetration of the cavity wall and wherein said penetrating member includes a distal end surface joined to a cylindrical body at a junction and said distal end of said portal sleeve includes a peripheral edge, said junction being aligned with said peripheral edge when said penetrating member and said portal sleeve move proximally during penetration of the cavity wall.

15. A retractable safety penetrating instrument as recited in claim 1 further including an inner member disposed within said penetrating member and having a distal end and means for permitting said inner member to move proximally in response to a proximal force from tissue contact at said distal end of said inner member during penetration of the cavity wall and to move distally thereafter and wherein said trigger means includes an operating member disposed on said inner member for actuating said retracting means in response to distal movement of said operating member.

16. A retractable safety penetrating instrument as recited in claim 15 wherein said penetrating member distal end is hollow and includes a distal end surface and said distal end of said inner member includes a distal end surface projecting beyond said penetrating member distal end surface, said distal end surface of said penetrating member being aligned with said distal end surface of said inner member when said inner member moves proximally during penetration of the cavity wall.

17. A retractable safety penetrating instrument as recited in claim 11 wherein said retracting means includes means for biasing said penetrating member proximally and said penetrating member carries an operating member thereon and further including a locking means engageable with said retracting means for preventing movement of said penetrating member proximally to said retracted position and trigger means including releasing means for being engaged by said operating member when said operating member moves distally with said penetrating member for disengaging said locking means from said retracting means.

18. A retractable safety penetrating instrument as recited in claim 17 wherein said locking means includes a latch biased into engagement with said retracting means.

19. A retractable safety penetrating instrument as recited in claim 17 wherein said latch includes a spring.

20. A retractable safety penetrating instrument as recited in claim 19 wherein said releasing means includes cam means for disengaging said latch from said retracting means.

21. A retractable safety penetrating instrument as recited in claim 20 wherein said trigger means is disposed on said cam means for being engaged by said operating member when said operating member moves distally.

22. A retractable safety penetrating instrument as recited in claim 21 wherein said cam means is biased to a rest position wherein said trigger means is disposed within the path of distal movement of said operating member.

23. A retractable safety penetrating instrument as recited in claim 19 wherein said releasing means includes a spring and said trigger means is disposed on said spring to be biased into the path of distal movement of said operating member.

24. A retractable safety penetrating instrument as recited in claim 18 wherein said latch includes a locking bar and said releasing means includes a spring for biasing said locking bar into engagement with said retracting means and for disengaging said locking bar from said retracting means and wherein said trigger means is biased into the path of distal movement of said operating member.

25. A retractable safety penetrating instrument as recited in claim 24 wherein said stop means is disposed on said locking bar.

26. A retractable safety penetrating instrument as recited in claim 17 wherein said locking means and said releasing means are of integral, unitary construction.

27. A retractable safety penetrating instrument as recited in claim 17 wherein said locking means and said releasing means are of multi-part construction.

\* \* \* \* \*